(12) United States Patent
Pizza et al.

(10) Patent No.: US 10,376,573 B2
(45) Date of Patent: Aug. 13, 2019

(54) VACCINES FOR SEROGROUP X MENINGOCOCCUS

(71) Applicants: GlaxoSmithKline Biologicals SA, Rixensart (BE); Institut Pasteur, Paris (FR)

(72) Inventors: Mariagrazia Pizza, Siena (IT); Peter Dull, Seattle, WA (US); Marzia Monica Giuliani, Siena (IT); Muhamed-Kheir Taha, Saint Maur des Fosses (FR); Eva Hong, Maisons-Alfort (FR); Ala-Eddine Deghmane, Gagny (FR)

(73) Assignees: GlaxoSmithKline Biologicals SA, Rixensart (BE); Institut Pasteur, Paris (FR)

( * ) Notice: Subject to any disclaimer, the term of this patent is extended or adjusted under 35 U.S.C. 154(b) by 44 days.

(21) Appl. No.: 14/407,987

(22) PCT Filed: Jun. 14, 2013

(86) PCT No.: PCT/IB2013/054886
§ 371 (c)(1),
(2) Date: Dec. 15, 2014

(87) PCT Pub. No.: WO2013/186753
PCT Pub. Date: Dec. 19, 2013

(65) Prior Publication Data
US 2016/0166674 A1   Jun. 16, 2016

Related U.S. Application Data

(60) Provisional application No. 61/659,595, filed on Jun. 14, 2012.

(51) Int. Cl.
*A61K 39/095* (2006.01)
*A61K 39/39* (2006.01)
*A61K 39/00* (2006.01)

(52) U.S. Cl.
CPC ........ *A61K 39/095* (2013.01); *A61K 2039/54* (2013.01); *A61K 2039/55505* (2013.01); *A61K 2039/70* (2013.01)

(58) Field of Classification Search
None
See application file for complete search history.

(56) References Cited

U.S. PATENT DOCUMENTS

| | | |
|---|---|---|
| 5,547,670 A | 8/1996 | Goldstein et al. |
| 6,013,267 A | 1/2000 | Blake et al. |
| 6,028,049 A | 2/2000 | Jacobs et al. |
| 6,180,111 B1 | 1/2001 | Stein et al. |
| 6,197,312 B1 | 3/2001 | Peak et al. |
| 6,709,660 B1 | 3/2004 | Scarlato et al. |
| 6,914,131 B1 | 7/2005 | Scarlato et al. |
| 7,348,006 B2 | 3/2008 | Contorni et al. |
| 7,368,261 B1 | 5/2008 | Rappuoli |
| 7,576,176 B1 | 8/2009 | Fraser et al. |
| 7,604,810 B2 | 10/2009 | Rappuoli |
| 7,731,967 B2 | 6/2010 | O'Hagan et al. |
| 7,785,608 B2 | 8/2010 | Zlotnick et al. |
| 7,862,827 B2 | 1/2011 | Giuliani et al. |
| 8,101,194 B2 | 1/2012 | Zlotnick et al. |
| 8,114,960 B2 | 2/2012 | Arico et al. |
| 8,226,960 B2 | 7/2012 | Masignani et al. |
| 8,273,360 B2 | 9/2012 | Pizza et al. |
| 8,293,251 B2 | 10/2012 | Scarlato et al. |
| 8,394,390 B2 | 3/2013 | Galeotti et al. |
| 8,398,988 B2 | 3/2013 | Contorni et al. |
| 8,398,999 B2 | 3/2013 | Masignani et al. |
| 8,470,340 B2 | 6/2013 | Beernink et al. |
| 8,524,251 B2 | 9/2013 | Fraser et al. |
| 8,563,007 B1 | 10/2013 | Zlotnick et al. |
| 8,574,597 B2 | 11/2013 | Zlotnick |
| 8,663,656 B2 | 3/2014 | Pizza |
| 8,703,914 B2 | 4/2014 | Arico et al. |
| 8,734,812 B1 | 5/2014 | Galeotti et al. |
| 8,765,135 B2 | 7/2014 | Contorni |
| RE45,137 E | 9/2014 | O'Hagan et al. |
| 8,834,888 B2 | 9/2014 | Contorni et al. |
| 8,840,907 B2 | 9/2014 | Pizza |
| 8,968,748 B2 | 3/2015 | Granoff et al. |
| 8,980,277 B2 | 3/2015 | Pizza |
| 8,980,286 B2 | 3/2015 | Comanducci |
| 9,011,869 B2 | 4/2015 | Pizza |

(Continued)

FOREIGN PATENT DOCUMENTS

| | | |
|---|---|---|
| CN | 1578785 A | 2/2005 |
| EP | 0011243 B1 | 4/1982 |

(Continued)

OTHER PUBLICATIONS

Kimura et al. Clinical and Vaccine Immunology vol. 18, No. 3, p. 482-486 Mar. 2011.*
Pinto et al. Vaccine 29 (2011) 7752-7758 Oct. 13, 2011 (available online Aug. 7, 2011).*
1997-11-17-NM_shotgun.dbs and 1997-12-15-NM.dbs, located at <ftp://ftp.sanger.ac.uk/pub/pathogens/nm/old data/> Generated Jul. 23, 2008. 2 pages.
741 ORF found using Sanger sequence with ORFFinder, accessed Aug. 5, 2009, submitted in the opposition proceedings for EP1801219. 5 pages.
Adams (1996). "Should Non-Peer-Reviewed Raw DNA Sequence Data Release Be Forced on the Scientific Community?," Science, 274: 534-536.

(Continued)

*Primary Examiner* — Oluwatosin A Ogunbiyi
(74) *Attorney, Agent, or Firm* — Morrison & Foerster LLP

(57) ABSTRACT

A method for immunizing a subject against serogroup X meningococcus by administering a vaccine comprising one, two or all three of: (i) a meningococcal fHbp antigen; (ii) a meningococcal NHBA antigen; and/or (iii) a meningococcal NadA antigen. The vaccine may also include meningococcal outer membrane vesicles.

13 Claims, No Drawings
Specification includes a Sequence Listing.

(56) References Cited

U.S. PATENT DOCUMENTS

| | | | |
|---|---|---|---|
| 9,056,075 B2 | 6/2015 | Pizza | |
| 9,067,987 B2 | 6/2015 | Galeotti et al. | |
| 9,139,621 B2 | 9/2015 | Fraser | |
| 9,150,898 B2 | 10/2015 | Arico | |
| 9,156,894 B2 | 10/2015 | Masignani et al. | |
| 9,206,399 B2 | 12/2015 | Adu-Bobie et al. | |
| 9,249,196 B2 | 2/2016 | Fraser et al. | |
| 9,364,528 B1 | 6/2016 | Giuliani et al. | |
| 9,468,673 B2 | 10/2016 | Pizza | |
| 9,526,776 B2 | 12/2016 | Baudner | |
| 9,610,342 B2 | 4/2017 | Giuliani | |
| 2002/0160016 A1 | 10/2002 | Peak et al. | |
| 2004/0092711 A1 | 5/2004 | Arico | |
| 2004/0110670 A1 | 6/2004 | Arico et al. | |
| 2004/0167068 A1 | 8/2004 | Zlotnick et al. | |
| 2005/0232936 A1 | 10/2005 | Arico et al. | |
| 2006/0051840 A1 | 3/2006 | Arico et al. | |
| 2006/0171957 A1 | 8/2006 | Pizza | |
| 2006/0240045 A1 | 10/2006 | Berthet et al. | |
| 2006/0251670 A1 | 11/2006 | Comanducci et al. | |
| 2007/0026021 A1 | 2/2007 | Fraser et al. | |
| 2007/0082014 A1 | 4/2007 | Costantino | |
| 2007/0253984 A1 | 11/2007 | Khandke et al. | |
| 2008/0248065 A1 | 10/2008 | Granoff et al. | |
| 2009/0035328 A1 | 2/2009 | Granoff | |
| 2009/0232820 A1 | 9/2009 | Fraser et al. | |
| 2009/0285845 A1 | 11/2009 | Masignani et al. | |
| 2010/0267931 A1 | 10/2010 | Arico et al. | |
| 2011/0020390 A1 | 1/2011 | Pizza et al. | |
| 2012/0070458 A1 | 3/2012 | Contorni et al. | |
| 2012/0107339 A1 | 5/2012 | Granoff et al. | |
| 2013/0236489 A1 | 9/2013 | Serruto et al. | |
| 2014/0037668 A1 | 2/2014 | Giuliani et al. | |
| 2014/0363462 A1 | 12/2014 | Arico et al. | |
| 2015/0079124 A1 | 3/2015 | Fraser et al. | |
| 2015/0086582 A1 | 3/2015 | Fraser et al. | |

FOREIGN PATENT DOCUMENTS

| | | | |
|---|---|---|---|
| EP | 0273116 A2 | 7/1988 | |
| EP | 0467714 A1 | 1/1992 | |
| EP | 1534326 A2 | 6/2005 | |
| EP | 1645631 B1 | 10/2007 | |
| EP | 2351767 A2 | 8/2011 | |
| EP | 1790660 B1 | 6/2012 | |
| NL | 8901612 A | 7/1990 | |
| RU | 2378010 C2 | 11/2007 | |
| WO | WO-90/06696 A2 | 6/1990 | |
| WO | WO-92/16643 A1 | 10/1992 | |
| WO | WO-95/33049 A2 | 12/1995 | |
| WO | WO-96/29412 A1 | 9/1996 | |
| WO | WO-97/13860 A1 | 4/1997 | |
| WO | WO-98/17805 A2 | 4/1998 | |
| WO | WO-98/18930 A2 | 5/1998 | |
| WO | WO-99/24578 A2 | 5/1999 | |
| WO | WO-99/36544 A2 | 7/1999 | |
| WO | WO-99/57280 A2 | 11/1999 | |
| WO | WO-00/22430 A2 | 4/2000 | |
| WO | WO-00/66741 A2 | 11/2000 | |
| WO | WO-00/66791 A1 | 11/2000 | |
| WO | WO-00/71725 A2 | 11/2000 | |
| WO | WO-01/31019 A2 | 5/2001 | |
| WO | WO-01/34642 A2 | 5/2001 | |
| WO | WO-01/52885 A1 | 7/2001 | |
| WO | WO-01/64920 A2 | 9/2001 | |
| WO | WO-01/64922 A2 | 9/2001 | |
| WO | WO-01/91788 A1 | 12/2001 | |
| WO | WO-02/09643 A2 | 2/2002 | |
| WO | WO-03/009869 A1 | 2/2003 | |
| WO | WO-03/010194 A2 | 2/2003 | |
| WO | WO-03/020756 A2 | 3/2003 | |
| WO | WO2003063766 A2 * | 8/2003 | |
| WO | WO-03/105890 A2 | 12/2003 | |
| WO | WO-2004/019977 A2 | 3/2004 | |
| WO | WO-04/032958 A1 | 4/2004 | |
| WO | WO-04/048404 A2 | 6/2004 | |
| WO | WO-2004/065603 A2 | 8/2004 | |
| WO | WO-2004/094596 A2 | 11/2004 | |
| WO | WO-2005/004908 A1 | 1/2005 | |
| WO | WO-051032583 A2 | 4/2005 | |
| WO | WO-05/106009 A2 | 11/2005 | |
| WO | WO2005/102384 A2 * | 11/2005 | |
| WO | WO-06/024954 A2 | 3/2006 | |
| WO | WO-2006/024946 A2 | 3/2006 | |
| WO | WO-2006/046143 A2 | 5/2006 | |
| WO | WO-2006/081259 A2 | 8/2006 | |
| WO | WO-2007/060548 A2 | 5/2007 | |
| WO | WO-2007/127665 A2 | 11/2007 | |
| WO | WO-2008/079372 A2 | 7/2008 | |
| WO | WO-2008/125985 A2 | 10/2008 | |
| WO | WO-2008/149238 A2 | 12/2008 | |
| WO | WO-2009/038889 A1 | 3/2009 | |
| WO | WO-2009/104097 A2 | 8/2009 | |
| WO | WO-2010/028859 A1 | 3/2010 | |
| WO | WO-2010/046715 A1 | 4/2010 | |
| WO | WO2010109325 * | 9/2010 | |
| WO | WO-2011/036562 A1 | 3/2011 | |
| WO | WO-2011051893 A1 | 5/2011 | |
| WO | WO-2011/110634 A1 | 9/2011 | |
| WO | WO-2011/126863 A1 | 10/2011 | |
| WO | WO-2012032489 A1 | 3/2012 | |
| WO | WO 2013/177397 * | 11/2013 | |

OTHER PUBLICATIONS

Aderson et al. (2010). "Effectiveness of a bivalent factor H binding protein vaccine across Neisseria meningitidis serogroups," 17th International Pathogenic Neisseria Conference 2010, p. 196.

Aebi et al. (1997). "A protective epitope of Moraxella catarrhalis is encoded by two different genes," Infect Immun. 65(11):4367-77.

Ala'Aldeen et al. (2010) "Human antibody response to the meningococcal factor H binding protein (LP2086) during invasive disease, colonization and carriage," Vaccine 28:7667-75.

Alignment of SEQ ID No. 19 of EP2327719 against SEQ ID Nos. 92, 94, 96, 98, 100, 102, 104, 106, and 108 of WO/2003/063766, filed in opposition against EP2327719, submitted May 20, 2015, 9 pages.

Alignment of SEQ ID No. 42 of EP2258716 against SEQ ID No. 41 of EP2258716, filed in opposition against EP2258716, submitted Apr. 16, 2015, 1 page.

Alignment of SEQ ID No. 42 of EP2258716 against SEQ ID Nos. 50, 52, 54, 56, 58, 60, 62, 64, 66, 68, 70, and 72 of WO/2003/063766, filed in opposition against EP2258716, submitted Apr. 16, 2015, 12 pages.

Ambrose et al. (2006). "Characterization of LP2086 expression in Neisseria meningitidis," 15th International Pathogenic Neisseria Conference 2006, p. 103.

Amended Defence and Counterclaim, Jul. 24, 2015, Claim No. HP-2015-000022, *Glaxosmithkline UK LTD* v. *Wyeth Holdings LLC*, 4 pages.

Anderson et al. (2008). "Functional cross-reactive antibodies are elicited by a group B Neisseria meningitidis bivalent recombinant lipidated LP2086 vaccine in cynomolgusmacaques," 16th International Pathogenic Neisseria Conference (IPNC) P100, pp. 170-171.

Anderson et al. (2009). "Development of a factor H binding protein vaccine for broad protection against invasive Neisseria meningitidis serogroup B (MnB) disease," 10th European Meningococcal Disease Society Congress 2009, p. 39.

Anderson et al. (2009). "Epidemiology of the serogroup B Neisseria meningitidis (MnB) factor H binding protein and implications for vaccine development," European Society for Paediatric Infectious Disease Symposium 2009, p. 505.

Anderson et al. (2012). "Potential impact of the bivalent rLP2086 vaccine on Neisseria meningitidis invasive disease and carriage isolates in two adolescent populations," European Society for Paediatric Infectious Disease Symposium 2012, p. 807.

Anderson et al. (2013) "Potential impact of the bivalent rLP2086 vaccine on Neisseria meningitidis carriage and invasive serogroup B disease," Hum Vacc Immunotherap 9:471-9.

(56) References Cited

OTHER PUBLICATIONS

Annex 1 to the Amended Defence and Counterclaim, Jun. 24, 2015, Claim No. HP-2015-000022, *Glaxosmithkline UK LTD* v. *Wyeth Holdings LLC*, 40 pages.
Appendix I to Statement of Grounds of Appeal filed by df-mp on Sep. 28, 2012, in relation to EP1645631, 1 page.
Appendix II to Statement of Grounds of Appeal filed by df-mp on Sep. 28, 2012, in relation to EP1645631, 2 pages.
Bai et al. (2011) "Recombinant protein meningococcal serogroup B vaccine combined with outer membrane vesicles." Expert Opin Biol Ther. 11:969-85.
Beernink (Jul. 2010) "Impaired immunogenicity of a meningococcal factor H-binding protein vaccine engineered to eliminate factor h binding," Clin Vac Immunol 17(7):1074-1078.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.
Beernink et al. (2009) "Meningococcal factor H-binding protein variants expressed by epidemic capsular group A, W-135, and X strains from Africa." J Infect Dis 199:1360-8.
Beernink et al. (2011). "A meningococcal factor H binding protein mutant that eliminates factor H binding enhances protective antibody responses to vaccination," J Immunol, 186(6):3606-14.
Beernink et al. (Jun. 2008). "Bactericidal antibody responses, induced by meningococcal recombinant chimeric factor H-binding protein vaccines," Infection and Immunity 76(6):2568-2575.
Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.
Ben Mohamed et al. (2002). "Lipopeptide vaccines-yesterday, today, and tomorrow," Lancet 2(7):425-431.
Bentley et al. (2004). Identification of two immunologically distinct domains on the LP2086 outer membrane lipoprotein of Neisseria meningitidis, 14th International Pathogenic Neisseria Conference 2004, p. 144.
Bernfield et al. (2002). "Identification of a novel vaccine candidate for group B Neisseria meningitidis," 13th International Pathogenic Neisseria Conference 2002, Poster, 20 pages.
Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, p. 116.
Biswas et al. (1995). "Characterization of IbpA, the structural gene for a lactoferrin receptor in Neisseria gonorrhoeae," Infection and Immunity, 63(8): 2958-2967.
Blattner et al. (1997). "The complete genome sequence of *Escherichia coli* K-12," Science 277(5331): 1453-1474.
Borrow et al. (2005) "Interlaboratory standardization of the measurement of serum bactericidal activity by using human complement against meningococcal serogroup b, strain 44/76-SL, before and after vaccination with the Norwegian MenBvac outer membrane vesicle vaccine." Clin Diag Lab Immunol 12:970-6.
Borrow et al. (2006) "Neisseria meningitidis group B correlates of protection and assay standardization—international meeting report Emory University, Atlanta, Georgia, United States, Mar. 16-17, 2005." Vaccine. 24:5093-107.
Boslego et al. (1991). "Gonorrhea Vaccines," Chapter 17 in *Vaccines and Immunotherapy*, Cryz S.J. (Ed.), Pergamon Press: New York, NY, pp. 211-223.
Bouvier et al. (1991). "A gene for a new lipoprotein in the dapA-purC interval of the *Escherichia coli* chromosome," J Bacteriol 173(17):5523-5531.
Bowe et al. (Jul. 2004) "Mucosal vaccination against serogroup B meningococci: induction of bacterial antibodies and cellular immunity following intranasal immunization with NadA of *Neisseria meningitides* and mutants of *Escherichia coli* heat-labile enterotoxin," Infection and Immunity, 72: 4052-4060.

Brendish and Read. (2015). "Neisseria meningitidis serogroup B bivalent factor H binding protein vaccine," Expert Rev. Vaccines, 14(4):493-503.
Cannon (1989). "Conserved Lipoproteins of Pathogenic *Neisseria* Species Bearing the H.8 Epitope: Lipid-Modified Azurin and H.8 Outer Membrane Protein," Clinical Microbiology Reviews 2(Suppl.):S1-S4.
Cantini et al. (Mar. 2006). "Solution Structure of the Immunodominant Domain of Protective Antigen GNA 1870 of Neisseria meningitidis," *Journal of Biological Chemistry* 281(11): 7220-7227.
Capecchi et al. (2005) "*Neisseria meningitides* NadA is a new invasion which promotes bacterial adhesion to and penetration into human epithelial cells," Molecular Microbiology, 55: 687-698.
CECMED (Dec. 2, 2011), "Resumen de las Caracteristicas del Producto: VA-MENGOC-BC," Ministerio de Salud Publica de Cuba, 4 pages. (3 page English translation included).
Chen, et al. (1994). "Determination of the optimal aligned spacing between the Shine-Dalgarno sequence and the translation initiation codon of *Escherichia coli* mRNAs," Nucleic Acids Res. 22(23):4953-4957.
Claimant's Amended Grounds of Invalidity under CPR 17.1 (2)(a) on Jul. 16, 2015, in respect of European Patent (UK) No. 2,343,308. In the High Court of Justice Chancery Division Patents Court, between GlaxoSmithKline UK Limited and Wyeth Holdings LLC. 9 pages.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1> 3 pages.
Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028&rank=1> 4 pages.
Clustal alignment of menA and menB sequences with upstream sequence, performed using Clustal on Genbank NC_003116.1 and NC_003112.2, no date. Submitted in opposition proceedings of EP1645631. 2 pages.
Cohn et al. (2010). "Potential Impact of Serogroup B Vaccines: Prevalence of candidate vaccine antigens among invasive Neisseria meningitidis isolates in the United States," 17th International Pathogenic Neisseria Conference 2010, p. 77.
Cole et al. (1998). "Deciphering the biology of *Mycobacterium tuberculosis* from the complete genome sequence," Nature 394:651-653.
Comanducci et al. (Jul. 2004) "NadA diversity and carriage in *Neisseria meningitides*," Infection and Immunity, 72: 4217-4223.
Comanducci, et al. (2002). "NadA, a Novel Vaccine Candidate of Neisseria Meningitides," Journal of Experimental Medicine 195(11):1445-1454.
Cordis, "Preparation of meningococcal antigens," posted online on Feb. 2, 2005, 2 pages.
Cruse et al. (2003). Illustrated Dictionary of Immunology, $2^{nd}$ Ed. CRC Press, pp. 46, 166, and 382.
Database accession No. NMB1994 (cf. XP2231040) (Tettelin et al.), uploaded Oct. 1, 2000. 337 pages.
Database UniProt ( Feb. 6, 2007). Submitted name: Putative lipoprotein, Uniprot accession No. A1IQ30, PIR No. G81977, retrieved Jan. 20, 2016 from <http://www.uniprotorg/uniprot/A1IQ30>, 7 pages.
Database UniProt (Oct. 1, 2000), "SubName: Full=Uncharacterized protein" retrieved from EBI, accession No. Q9JXV4 Database accession No. Q9JXV4, PIR No. D81032, 2 pages.
de Moraes JC, et al. (1992). Protective efficacy of a serogroup B meningococcal vaccine in Sao Paulo, Brazil. Lancet 340: 1074-1078.
Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).
Decision of Technical Board of Appeal for EP942983, dated Nov. 14, 2013, filed in relation to EP1645631, 28 pages.

(56) References Cited

OTHER PUBLICATIONS

Decision revoking EP1737486, filed in opposition against EP1737486, dated Oct. 28, 2015, 28 pages.
Decision revoking the European Patent, filed in opposition against EP1976990, dated Nov. 11, 2013, 15 pages.
Decision to refuse a patent application, filed in the Opposition against EP1645631, dated Apr. 28, 2009, 7 pages.
Declaration by Dr. Ellen Murphy, Ph.D., dated Sep. 14, 2011, submitted in opposition proceedings for EP1645631, 4 pages.
Declaration by Dr. Julian Parkhill dated Jun. 12, 2008, submitted in opposition proceedings for EP1645631, 2 pages.
Declaration by Dr. Julian Parkhill, filed in the Opposition against EP1645631, dated Jul. 10, 2014, 5 pages.
Declaration by E. Richard Moxon dated Feb. 16, 2013, submitted in opposition proceedings for EP1645631, 5 pages.
Declaration by Ellen Murphy, filed in the Opposition against EP1645631, dated May 12, 2014, 3 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by Prof. Paul Dunman, Ph.D., dated Sep. 13, 2011, submitted in opposition proceedings for EP1801219, 10 pages.
Declaration by Prof. Paul Dunman, Ph.D., dated Sep. 25, 2012, submitted in opposition proceedings for EP1645631, 14 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Delgado et al. (2007). "Lipoprotein NMB0928 from Neisseria meningitidis serogroup B as a novel vaccine candidate," Vaccine 25:8420-8431.
Dintilhac and Claverys (1997). "The adc locus, which affects competence for genetic transformation in *Streptococcus pneumoniae*, encodes an ABC transporter with a putative lipoprotein homologous to a family of streptococcal adhesins," Res Microbiol 148:119-131.
Dlawer et al. (2010). "Human antibody responses to the meningococcal factor H binding protein LP2086 during invasive disease," 17th International Pathogenic Neisseria Conference 2010, p. 130.
Donnelly et al. (2010). "Qualitative and quantitative assessment of meningococcal antigens to evaluate the potential strain coverage of protein-based vaccines," Proc Natl Acad Sci U S A, 107(45):19490-5.
Elzanowski et al. (2013). "The Genetic Codes, a compilation," Retrieved from http://www.bioinformatics.org/JaMBW/2/3/TranslationTables.html. 16 pages.
Experimental data: expression of NspA, fHBP and GNA2132 in N. meningitidis, filed in opposition against EP1534326, dated Aug. 4, 2010. 2 pages.
Experimental Report, Submitted on Mar. 23, 2015, filed in relation to EP2411048, 2 pages.
Facts and Submissions dated May 21, 2012, in relation to EP1645631, 30 pages.
Farley et al. (2002). "Characterization, cloning and expression of different subfamilies of the ORF 2086 gene from Neisseria meningitidis," 13th International Pathogenic Neisseria Conference 2002, Poster, 15 pages.
Farley J. et al. (Sep. 2002). "Characterization, cloning and expression of different subfamilies of the ORF 2086 gene from Neisseria meningitidis," Thirteenth International Pathogenic Neisseria Conference, Norwegian Institute of Public Health, Oslo, Norway, p. 124.
Feavers et al. (2009). "Meningococcal protein antigens and vaccines," Vaccine 275:B42-B50.
Fleischmann et al. (1995). "Whole-Genome Random Sequencing and Assembly of Haemophilus influenzae Rd," Science 269:496-512.
Fletcher et al. (2004). "Vaccine Potential of the Neisseria meningitidis 2086 Lipoprotein," *Infection and Immunity* 72(4): 2088-2100.

Fontana et al. (2002). A genomic approach Abstract from the 13th International Pathogenic Neisseria Conference, Oslo, Norway, Sep. 1-6, 2002. p. 248.
Frasch, C. et al. (Jun. 2009) "Bactericidal Antibody is the Immunologic Surrogate of Protection Against Meningococcal Disease," Vaccine 27( Suppl 2):B112-B116.
Fraser et al. (1997). "Genomic sequence of a lyme disease spirochaete, Borrelia burgdorferi," Nature 390:580-586.
Fraser et al. (1998). "Complete genome sequence of Treponema pallidum, the syphilis spirochete," Science 281:375-388.
Fukasawa, Lucila O. et al, (2003) "Immune response to native NadA from Neisseria meningitidis and its expression in clinical isoalted in Brazil." Journal of Medical Microbiology, vol. 52, pp. 121-125.
Further submissions by patentee, dated Feb. 3, 2016, filed in relation to EP1645631 appeal, 9 pages.
Further Submissions in the opposition against EP1801219, filed on behalf of Pfizer Inc. dated Jul. 14, 2016. 3 pages.
Gagneux et al. (2002) "Clonal groupings in serogroup X Neisseria meningitidis." Emerging Infect Dis 8:462-6.
Galeano et al. (1995). "Efectividad de una vacuna antimeningococcica en una cohorte de itagui, Colombia, 1995," Epidemiologico de Antioquia 20(2), 8 pages. (9 page English translation included).
Gene Browser, Nature Technology Corporation, filed in the Opposition against EP1645631, dated Jun. 26, 2013, 6 pages.
GenPept accession No. AAF42204, "hypothetical protein NMB1870 [Neisseria meningitidis MC58]," retrieved on Sep. 26, 2012, 2 pages.
Gervais et al. (1992). "Putative Lipoprotein Yaec Precursor," Database Swissprot Acc No. p28635.
Gil et al. (2009). "Proteomic study via a non-gel based approach of meningococcal outer membrane vesicle vaccine obtained from strain CU385," Human Vaccines 5(5):347-356.
Giuliani et al. (2006). "A universal vaccine for serogroup B meningococcus," PNAS 103(29):10834-10839.
Giuliani et al. (2010). "Measuring antigen-specific bactericidal responses to a multicomponent vaccine against serogroup B meningococcus," Vaccine 28:5023-5030.
Giuliani et al. (Feb. 2005). "The Region Comprising Amino Acids 100 to 255 of Neisseria meningitidis Lipoprotein GNA 1870 Elicits Bactericidal Antibodies," *Infection and Immunity* 73(2): 1151-1160.
Gold and Stormo (1987). "Translation Initiation", in *Escherichia con* and *Salmonella typhimurium*, Cellular and Molecular Biology, Ed. Neidhardt, pp. 1302-1307.
Gorringe & Pajon (2012) "Bexsero: a multicomponent vaccine for prevention of meningococcal disease." Human Vaccines & Immunotherapeutics 8:1-10.
Gorringe et al. (2009). "16th International Pathogenic Neisseria Conference: recent progress towards effective meningococcal disease vaccines," Human Vaccines 5(2):53-56.
Grandi (2005). "Reverse vaccinology: a critical analysis," in Encyclopedia of Genetics, Genomics, Proteomics and Bioinformatics, pp. 1322-1326.
Granoff, DM. (2009). Relative importance of complement-mediated bactericidal and opsonic activity for protection against meningococcal disease. Vaccine 27(Supplement 2): B117-B125.
Harris et al. (2008). "Development and qualification of serum bactericidal assays for Neisseria meningitidis serogroup B," 16th International Pathogenic Neisseria Conference 2008, p. 268-269.
Harris et al. (2010). "Robustness of the Serum Bactericidal Activity (SBA) Assay for Neisseria meningitidis serogroup B," 17th International Pathogenic Neisseria Conference 2010, p. 169.
Harris et al. (2011) "Preclinical evidence for the potential of a bivalent fHBP vaccine to prevent Neisseria meningitidis serogroup C disease," Human Vaccines 7:1 (suppl) 1-7.
Hayashi and Wu, "Identification and characterization of lipid-modified proteins in bacteria," Chapter 10 in Lipid Modifications of Proteins: A Practical Approach, Hooper and Turner (eds.), published in 1992, 27 pages.
Hem et al. (1995). "Structure and properties of aluminum-containing adjuvants," Vaccine Design. Subunit and Adjuvant Approach, pp. 249-276.

(56) References Cited

OTHER PUBLICATIONS

Hodge et al. (2006). "Development of a luminex-based meningococcal rLP2086-specific human IgG assay," 15th International Pathogenic Neisseria Conference 2006, p. 113.
Hoiseth et al. (2008). "LP2086 and MLST distribution in epidemiologically relevant strains of serogroup B Neisseria meningitidis," 16th International Pathogenic Neisseria Conference 2008, p. 205.
Hoist et al. (2014). "Variability of genes encoding surface proteins used as vaccine antigens in meningococcal endemic and epidemic strain panels from Norway," Vaccine 32:2722-2731.
Hou et al. (2005) "Protective antibody responses elicited by a meningococcal outer membrane vesicle vaccine with overexpressed genome-derived neisserial antigen 1870," J Infect Dis 192(4):580-90.
Hung et al. (2011). "The Neisseria meningitidis macrophage infectivity potentiator protein induces cross-strain serum bactericidal activity and is a potential serogroup B vaccine candidate," Infect Immun 79(9):3784-3791.
Interlocutory decision in opposition proceedings, filed in the Opposition against EP1645631, dated May 21, 2012, 82 pages.
Jacobsson et al. (2009). "Prevalence and sequence variations of the genes encoding the five antigens included in the novel 5CVMB vaccine covering group B meningococcal disease" Vaccine. 27:1579-1584.
Jansen et al. (2008). "Bivalent recombinant LP2086 vaccine to provide broad protection against Neisseria meningitidis B disease: immunological correlates of protection and how to assess coverage against invasive MnB strains," 16th International Pathogenic Neisseria Conference 2008, p. 80-81.
Jansen et al. (2009). "Development of a bivalent factor H binding protein vaccine to broadly protect against invasive Neisseria meningitides serogroup B (MnB) disease," European Society for Paediatric Infectious Disease Symposium 2009, p. 311.
Jansen et al. (2010). "Estimating effectiveness for Neisseria meningitidis serogroup B (MnB) vaccine candidates composed of non-serogroup specific antigens," 17th International Pathogenic Neisseria Conference 2010, p. 37.
Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.
JCVI-CMR website showing Z2491 Sanger sequence (http://cmr.jcvi.org/tigr-scripts/CMR/shared/Genomes.cgi and links). (2010) 8 pages.
Jiang et al. (2003). "Using rate of acid neutralization to characterize aluminum phosphate adjuvant," Pharma Dev Tech 8(4):349-356.
Jiang et al. (2006). "Serum IgG response induced by a bivalent recombinant LP2086 provides broad protection against serogroup B Neisseria meningitidis," 15th International Pathogenic Neisseria Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic Neisseria Conference 2008, p. 57-58.
Jiang et al., (2010) "Broad vaccine coverage predicted for a bivalent recombinant factor H binding protein based vaccine to prevent serogroup B meningococcal disease" Vaccine 28:6086-6093.
Johnson et al. (1999). "Analysis of the human Ig isotype response to lactoferrin binding protein A from Neisseria meningitidis," FEMS Immun. Med. Microbial. 25(4): 349-354.
Jones et al. (2009). "Generation of human serum complement lots that perform consistently for use in Neisseria meningitidis serogroup B (MnB) vaccine clinical trials," European Society for Paediatric Infectious Disease Symposium 2009, p. 566.
Juncker et al. (2003). "Prediction of lipoprotein signal peptides in gram-negative bacteria," Protein Sci 12:1652-1662.
Koeberling et al. (2007). "Improved immunogenicity of a H44/76 group B outer membrane vesicle vaccine with over-expressed genome-derived Neisserial antigen 1870," Vaccine 25(10):1912-1920.

Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Kovacs-Simon et al. (2011). "Lipoproteins of Bacterial Pathogens," Infect Immun 79(2):548-561.
Legrain et al. (1995). "Production of Lipidated Meningococcal Transferrin Binding Protein 2 in *Escherichia coli*," Protein Expression and Purification 6:570-578.
Lewis et al. (2010). "The meningococcal vaccine candidate neisserial surface protein A (NspA) binds to factor H and enhances meningococcal resistance to complement," PLoS Pathogens 6(7):e1001027. 20 pages.
Liebl et al. (1997). "Properties and gene structure of the Thermotoga maritima alpha-amylase AmyA, a putative lipoprotein of a hyperthermophilic bacterium," J Bacteriol 179(3):941-948.
Liechti et al. (2012). "Outer membrane biogenesis in *Escherichia coli*, Neisseria meningitidis, and Helicobacter pylori: paradigm deviations in H. pylori," Front Cell and Infect Microbiol 2:article 29. 18 pages.
Lindblad, (2004). "Aluminium compounds for use in vaccines," Immunol Cell Biol.,82(5):497-505.
Litt et al. (2004). "Putative vaccine antigens from Neisseria meningitidis recognized by serum antibodies of young children convalescing after meningococcal disease," J Infect Dis 190(8):1488-97.
Lucidarme et al., (2010). "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Madico et al. (2006). "The meningococcal vaccine candidate GNA1870 binds the complement regulatory protein factor H and enhances serum resistance," J Immunol 177(1):501-510.
Magagnoli et al. (2009). "Structural organization of NadADelta(351-405), a recombinant MenB vaccine component, by its physicochemical characterization at drug substance level," Vaccine, 27(15):2156-70.
Marshall et al. (2008). "A randomized, placebo-controlled, double-blind, phase 1 trial of ascending doses of meningococcal group B rLP2086 vaccine in healthy adults," 16th International Pathogenic Neisseria Conference 2008, p. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.
Marshall et al. (2013) "A phase 2 open-label safety and immunogenicity study of a meningococcal B bivalent rLP2086 vaccine in healthy adults," Vaccine 31:1569-75.
Martin et al. (1998). "New Zealand epidemic of meningococcal disease identified by a strain with phenotype B:4:P1.4," JID 177:497-500.
Martin et al. (2003). "Experimentally revised repertoire of putative contingency loci in *Neisseria meningitidis* strain MC58: evidence for a novel mechanism of phase variation," Molecular Microbiology 50(1):245-257.
Mascioni et al. (2008). "Determination of the domain and solution structure of rLP2086, a meningococcal vaccine candidate and human factor H binding protein," 16th International Pathogenic Neisseria Conference 2008, p. 77-78.

(56) References Cited

OTHER PUBLICATIONS

Mascioni et al. (2009) "Structural basis for the immunogenic properties of the meningococcal vaccine candidate LP2086," J Biol Chem 284:8738-46.
Mascioni et al. (2010) "NMR dynamics and antibody recognition of the meningococcal lipidated outer membrane protein LP2086 in micellar solution," Biochim Biophys Acta 1798:87-93.
Masignani V. (Mar. 17, 2003). "Vaccination against Neisseria meningitidis using three variants of the lipoprotein GNA1870," J. Exp. Med. 197(6):789-799.
McNeil et al. (2009) "Detection of LP2086 on the cell surface of Neisseria meningitidis and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic Neisseria Conference 2010, p. 94.
McNeil et al. (2013) "Role of factor H binding protein in Neisseria meningitidis virulence and its potential as a vaccine candidate to broadly protect against meningococcal disease," Microbiol Mol Biol Rev 77:234.
Meyer et al. (1984). "Pilus genes of Neisseria gonorrheae: Chromosomal organization and DNA sequence," Proc. Natl. Acad. Sci. USA 81: 6110-6114.
Milagres et al. (1998). "Specificity of bactericidal antibody response to serogroup B meningococcal strains in Brazilian children after immunization with an outer membrane vaccine," Infection and Immun. 66(10): 4755-4781.
Minutes of the oral proceedings, filed in the Opposition against EP1645631, dated Feb. 11, 2014, 4 pages.
Morley, S. et al. (Dec. 12, 2001). "Vaccine prevention of meningococcal disease, coming soon?" *Vaccine* 20(5-6):666-687.
Munkley, et al. (1991). "Blocking of bactericidal killing of Neisseria meningitidis by antibodies directed against slacc 4 outer membrane proteins," Microbial Pathogenesis 11: 447-452.
Murphy et al. (2008). "Sequence diversity of vaccine candidate LP2086 in Neisseria meningitidis serogroup B strains causing invasive disease," 16th International Pathogenic Neisseria Conference 2008, p. 61.
Murphy et al. (2010). "Prevalence of Factor H Binding Protein (fHBP) Variants in N. meningitidis Carriage Isolates," 17th International Pathogenic Neisseria Conference 2010, p. 96.
Murphy et al., (2009) "Sequence diversity of the factor H binding protein vaccine candidate in epidemiologically relevant strains of serogroup B Neisseria meningitidis" J Infect Dis 200:379-389.
Nassif (2000). "A Furtive Pathogen Revealed," Science 287:1767-1768.
Notice of Opposition against EP 1562983, filed on Jul. 1, 2014, 23 pages.
Notice of Opposition against EP1645631, filed in the Opposition against EP1645631, dated Jul. 23, 2008, 25 pages.
Notice of Opposition against EP1801219, filed on behalf of Pfizer Inc. dated Jul. 14, 2016. 54 pages.
Notice of opposition against EP2343308, filed in opposition against EP1562983, submitted Jan. 11, 2016, 21 pages.
Notice of Opposition filed May 24, 2012, filed in opposition against EP1976990, 19 pages.
Notice of opposition, filed in opposition against EP2258716, dated Apr. 16, 2015, 12 pages.
Notice of opposition, filed in opposition against EP2327719, dated May 20, 2015, 14 pages.
Novartis (Jan. 22, 2013) "Novartis receives EU approval for Bexsero®, first vaccine to prevent the leading cause of life-threatening meningitis across Europe," Media Release, 3 pages.
Novartis (Jun. 9, 2011). "Novartis candidate vaccine Bexsero® shows significant potential in providing broad coverage against meningococcal serogroup B infections." Media Release, 6 pages.
Novartis (Oct. 9, 2008) "New Phase II data show Novartis investigational Meningitis B vaccine may also protect infants six months and older," Media Release, 4 pages.
Novartis internal data, filed in relation to EP1902726, submitted on Apr. 13, 2015, 1 page.
Ochoa, Rolando (2008). "Main projects on research, development and manufacturing of human vaccines," excerpt from presentation at BioQatar Symposium 2008, 4 slides.
Opponent's Further Submission in Preparation of the Oral Proceedings, filed in the Opposition against EP1645631, dated Nov. 3, 2011, 6 pages.
Opponent's Response to the Patentee's Grounds of Appeal, filed in the Opposition against EP1737486 on Jul. 20, 2016, 19 pages.
Opponent's Response to the Patentee's Submission dated Feb. 18, 2013, filed in the Opposition against EP1645631, dated Jul. 24 2014, 34 pages.
Opponents Final Written Submission in Preparation of Oral Proceedings, filed in the Opposition against EP1645631, dated Sep. 14, 2011, 28 pages.
ORF Finder (2013). "Bacterial Code," Retrieved from http://www.ncbi.nlm.nih.gov/gorf/gorf.html, 3 pages.
ORF Finder result for NMB1870 sequence with upstream sequence, chromosome ASM880v1, accessed Sep. 27, 2012, submitted in the opposition proceedings for EP1801219. 2 pages.
Pajon et al. (2010). "Frequency of factor H-binding protein modular groups and susceptibility to cross-reactive bactericidal activity in invasive meningococcal isolates" Vaccine 28:2122-2129.
Pajon et al. (2012). "Design of meningococcal factor H binding protein mutant vaccines that do not bind human complement factor H," Infect Immun 80:2667-2677.
Parkhill et al. (2000). "Complete DNA Sequence of a Serogroup A Strain of Neisseria meningitides Z2491," Nature, 404(6777):502-506.
Parkhill, "Campylobacter jejuni genome sequence at the Sanger Centre," Post on BIOSCI/Bionet of May 8, 1998. 1 page.
Patentee's response to notice of opposition, filed in opposition against EP1562983, dated Feb. 16, 2015, 9 pages.
Patentee's Submissions under Rule 116 EPC, filed in the Opposition against EP1645631, dated Sep. 13, 2011, 13 pages.
Patentees' Response to Opposition, filed in opposition against European Patent EP1645631, dated May 8, 2009, 13 pages.
Perez et al. (2010). "Community acquired bacterial meningitis in Cuba: a follow up of a decade," BMC Infectious Diseases 10:130, 9 pages.
Pettersson, et al. (2006). "Vaccine potential of the Neisseria meningitidis lactoferrin-binding proteins LbpA and LbpB," Vaccine 24(17):3545-3557.
Pfizer observations, filed in opposition against EP1562983, dated Apr. 27, 2012, 7 pages.
Pfizer observations, filed in opposition against EP1562983, dated May 12, 2011, 7 pages.
Pillai et al. (2005) "Outer membrane protein (OMP) based vaccine for Neisseria meningitidis serogroup B," Vaccine 23(17-18):2206-2209.
Pizza et al. (2000). "Identification of Vaccine Candidates Against Serogroup B Meningococcus by Whole-Genome Sequencing," Science 287(5459):1816-1820.
Pizza et al. (2008) "Factor H-binding protein, a unique meningococcal vaccine antigen" Vaccine 26S:I46-8.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Priority document for U.S. Appl. No. 60/162,616, filed Oct. 29, 1999. 1 page.
Progress through the Sanger Institute FTP server (May 12, 2009), 15 pages.
Prosite Analysis of the sequence related to orf741 from D5 I D20 I D20a with Prosite (www.prosite.expasy.org), accessed Jun. 21, 2012, submitted in the opposition proceedings for EP1801219. 1 page.
Prosite, "ScanProsite Results Viewer: USERSEQ1 (280aa)," retrieved on Jun. 21, 2012, 1 page.

(56) References Cited

OTHER PUBLICATIONS

PSORT analysis of 200 of the sequences disclosed in PCT/US99/09346 (Jan. 1, 2010), 209 pages.
PSORT analysis of SEQ ID Nos. 4 and 6, and of 'Contig295' 300mer (May 8, 2009), 5 pages.
PSORT analysis of the sequence related to orf741 from the 'second' ATG, "D5 / D20 / D20A ORF", accessed Jun. 22, 2012, submitted in the opposition proceedings for EP1801219. 1 page.
PSORT analysis of the sequence related to orf741 from the 'second' ATG, "MENB 'Second' ATG Start" accessed Sep. 27, 2012, submitted in the opposition proceedings for EP1801219. 1 page.
PSORT prediction result for SEQ ID No. 2 (Mar. 30, 2010), 1 page.
Pugsley (1993). "The complete general secretory pathway in gram-negative bacteria," Microbiological Rev 5(1):50-108.
Renauld-Mongenie et al. (1997). "Identification of Human Transferrin-Binding Sites Within Meningococcal Transferrin-Binding Protein B," J. Bacteriology 197(20):6400-6407.
Response by opponent, filed in opposition against EP1562983, dated Jan. 11, 2016, 12 pages.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Response to Communication, filed in EP Application No. 07075161.5, dated Oct. 28, 2009. 2 pages.
Response to Notice of Opposition by Novartis Vaccines and Diagnostics SRL for EP2327719, dated Jan. 6, 2016. 10 pages.
Response to Notice of Opposition, filed in opposition against EP2258716, dated Dec. 3, 2015, 8 pages.
Result from "Hphob. / Hopp & Woods" using the SEQ ID No. 4 and SEQ ID No. 6 from WO 99/57280, accessed Jul. 13, 2016, submitted in the opposition proceedings for EP1801219. 4 pages.
Richmond et al. (2008). "A randomized, observer-blinded, active control, phase 1 trial of meningococcal serogroup B rLP2086 vaccine in healthy children and adolescents aged 8 to 14 years," 16th International Pathogenic Neisseria Conference 2008, p. 270-271.
Richmond et al. (2010). "Safety & immunogenicity of serogroup B Neisseria meningitidis (MnB) rLP2086 vaccine in adults and adolescent subjects: overview of 3 clinical trials," 17th International Pathogenic Neisseria Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent Neisseria meningitidis recombinant lipidated factor H binding protein vaccine in young adults: Results of a randomized, controlled, dose-escalation phase 1 trial," Vaccine 30(43):6163-74.
Richmond et al. (2012) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Rinaudo et al. (2009). "Vaccinology in the genome era", The Journal of Clinical Investigation, 119(9):2515-2525.
Rodriguez et al. (1999). "The epidemiological impact of antimeningococal B vaccination in Cuba," Mem Inst Oswaldo Cruz 94(4):433-440.
Sandbu et al. (2007). "Immunogenicity and safety of a combination of two serogroup B meningococcal outer membrane vesicle vaccines," Clin Vaccine Immunol, 14(9):1062-9.
Sanger Centre's "Projects" website as of Dec. 10, 1997 as retrievable via http://web.archive.org. 1 page.
Scarselli et al. (Feb. 13, 2009). "Epitope Mapping of a Bactericidal Monoclonal Antibody against the Factor H Binding Protein of Neisseria meningitides," Journal of Molecular Biology 386(1):97-108.
Schneider et al. (Apr. 16, 2009) "Neisseria meningitidis recruits factor H using protein mimicry of host carbohydrates," Nature 458(7240):890-893.
Seeber et al. (1991). "Predicting the adsorption of proteins by aluminum-containing adjuvants," Vaccine 9(3):201-203.
Seib et al. (2010). "Influence of serogroup B meningococcal vaccine antigens on growth and survival of the meningococcus in vitro and in ex vivo and in vivo models of infection," Vaccine 28(12):2416-2427.
Seib et al. (2011). "Characterization of Diverse Subvariants of the Meningococcal Factor H (fH) Binding Protein for Their Ability to Bind fH, to Mediate Serum Resistance, and to Induce Bactericidal Antibodies," Infect Immun, 79(2):970-81.
Sequence for "Putative Lipoprotein [Neisseria meningitidis Z2491]," NCBI Reference Sequence: YP_002342062.1, Mar. 30, 2000. 2 pages.
Sequence NMA0586 from "'741 ORF found using Sanger sequence with ORFFinder", with upstream sequence from Bacterial Emsembl, no date. Submitted in the opposition proceedings for EP1801219. 2 pages.
Serruto et al. (2009). "Genome-based approaches to develop vaccines against bacterial pathogens," Vaccine 27:3245-3250.
Serruto et al. (2010). "Neisseria meningitidis GNA2132, a heparin-binding protein that induces protective immunity in humans," PNAS 107(8):3770-3775.
Sheldon et al. (2011). "Phase 1, Randomized, Open-Label, Study to Assess the Safety and Immunogenicity of Serogroup B Neisseria Meningitidis (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of Erwinia chrysanthemi 3937," Mole Microbiol 19(3):455-466.
Sierra GV, et al. (1991). Vaccine against group B Neisseria meningitidis: protection trial and mass vaccination results in Cuba. NIPH Ann 14: 195-207.
Sprengart et al. (1997). "Functional importance of RNA interactions in selection of translation initiation codons," Molecular Microbiology, 24(1): 19-28.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Statement of Grounds of Appeal, dated Mar. 23, 2015, filed in relation to EP2411048, 8 pages.
Statement of grounds of appeal, dated Mar. 7, 2016, filed in relation to EP1737486, 9 pages.
Statement of grounds of appeal, filed in relation to EP1902726, dated Apr. 13, 2015, 9 pages.
Statement of Grounds of Appeal, filed in relation to EP2353608, dated Jul. 22, 2015, 8 pages.
Submission in opposition proceedings by Carpmaels and Ransford filed in EP1737486 on Jun. 12, 2015, 2 pages.
Submission in opposition proceedings by Pfizer Inc. filed against EP1737486 on Jun. 12, 2015, 7 pages.
Submission of the Patentee of Jul. 6, 2012, filed Jun. 24, 2014, in the Opposition against EP1645631, 4 pages.
Summons to Attend Oral Hearings dated May 3, 2016, for EP2275129, 8 pages.
Summons to oral proceedings pursuant to Rule 115(1) EPC, filed in the Opposition against EP1645631, dated Nov. 11, 2013, 12 pages.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Supplementary declaration by Ellen Murphy dated Sep. 26, 2012, submitted in opposition proceedings for EP1645631, 3 pages.
Supplementary material Table and Figure for "NM0586" of Parkhill et al., 2000, Nature. 28 pages.
Supplementary Submission to the Grounds of Appeal, filed in the Opposition against EP1645631, dated Sep. 28, 2012, 2 pages.

(56) References Cited

OTHER PUBLICATIONS

Sutcliffe and Russell (1995). "Lipoproteins of gram-positive bacteria," J Bacteriol 177(5):1123-1128.
Swaminathan (1996). "Molecular cloning of the three base restriction endonuclease R.CviJl from eukaryotic Chlorella virus IL-3A," Nucleic Acids Research, 24(13): 2463-2469.
Sworn Statement in EP1645631 from Isabel Delany, signed Feb. 1, 2016. 2 pages.
Tan et al. (2010). "Advances in the development of vaccines against Neisseria meningitidis," NEJM 362(16):1511-1520.
Tavano et al. (2011). "Mapping of the Neisseria meningitidis NadA cell-binding site: Relevance of predicted α-helices in the NH2-terminal and dimeric coiled-coil regions," J Bacteriol 193(1):107-115.
Tavano et al. (Jul. 2000). "The membrane expression of Neisseria meningitidis adhesin A (NadA) increases the proimmune effects of MenB OMVs on human macrophages, compared with NadA-OMVs, without further stimulating their proinflammatory activity on circulating monocytes," J Leukoc Biol 86(1):143-153.
Telford et al. (2003). "Genomic and Proteomics in Vaccine Design", in *New Bacterial Vaccines* edited by Ellis et al. Kleweur Academic/Plenum Publishers, USA. pp. 1-11.
Tettelin et al. (Mar. 10, 2000). "Complete Genome Sequence of Neisseria meningitidis Serogroup B Strain MC58," Science 287(5459):1809-1815.
The printed output from the NCBI open reading frame finder (Oct. 20, 2008), 12 pages.
TIGR Microbial Database, filed in the Opposition against EP1645631, dated Jun. 20, 2012, 14 pages.
TIGR website as of 1998, 8 pages.
Tramont, (1976) "Specificity of inhibition of epithelial cell adhesion of Neisseria gonorrhoeae." Infection and Immunity 14:593-595.
Turner et al. (2006). "Characterization of MspA, an Immunogenic Autotransporter Protein That Mediates Adhesion of Epithelial and Endothelial Cells in *Neisseria meningitidis*," Infection and Immunity 74(5):2957-2964.
UniProt accession No. C0JF81, Murphy et al., Last modified on May 5, 2009. 4 pages.
United States Office Action dated Feb. 11, 2009, for U.S. Appl. No. 10/181,600, filed Jan. 17, 2001, 5 pages.
United States Office Action dated Jul. 24, 2008, for U.S. Appl. No. 10/181,600, filed Jan. 17, 2001, 23 pages.
United States Office Action dated Jul. 7, 2009, for U.S. Appl. No. 10/181,600, filed Jan. 17, 2001, 23 pages.
U.S. Appl. No. 60/098,685, "*Neisseria* Spp, Polypeptide, Gene Sequence and Uses Thereof," filed Sep. 1, 1998. 82 pages.
U.S. Appl. No. 60/328,101, "Novel immunogenic compositions for the prevention and treatment of meningococcal disease," filed Oct. 11, 2001. 253 pages.
U.S. Appl. No. 60/406,934, "Novel immunogenic compositions for the prevention and treatment of meningococcal disease," filed Aug. 30, 2002. 190 pages.
U.S. Appl. No. 60/647,911, "GNA 1870-based vesicle vaccines for broad spectrum protection against diseases caused by Neisseria meningitidis," filed Jan. 27, 2005. 99 pages.
U.S. Appl. No. 61/358,816, "Combinations of Meningococcal Factor H Binding Proteins," filed Jun. 25, 2010. 48 pages.
Van der Lay et al. (1995). "Construction of Neisseria Meningitidis Strains Carrying Multiple Chromosomal Copies of the PorA Gene for Use in Production of a Multivalent Outer Membrane Vesicle Vaccine," *Vaccine* 13(4): 401-407.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.
von Heijne (1989). "The structure of signal peptides from bacterial lipoproteins," Protein Engineering 2(7):531-534.
Voulhoux and Tommassen (2002). "Transport of lipoproteins to the cell surface in Neisseria meningitidis," 13th International Pathogenic Neisseria Conference 2002, p. 31.
Wang et al. (2010). "Prevalence and genetic diversity of candidate vaccine antigens among invasive Neisseria meningitidis isolates in the United States," 17th International Pathogenic Neisseria Conference 2010, p. 122.
Welsch et al. (2002). "Genome-derived antigen (GNA) 2132 elicits protective serum antibodies to groups B and C Neisseria meningitidis strains," 13th International Pathogenic Neisseria Conference 2002, p. 25.
Welsch et al. (2003). "Antibody to genome-derived neisserial antigen 2132, a Neisseria meningitidis candidate vaccine, confers protection against bacteremia in the absence of complement-mediated bactericidal activity" Journal of Infectious Diseases 188 (11):1730-1740.
Welsch et al. (2004). "Protective Activity of Monoclonal Antibodies to Genome-Derived Neisserial Antigen 1870, a Neisseria meningitidis Candidate Vaccine," *The Journal of Immunology* 172: 5606-5615.
Welsch et al. (2007) "A novel mechanism for complement-mediated killing of encapsulated Neisseria meningitidis elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Written Submission to Oral Proceedings, filed in opposition against EP1976990, dated Jul. 24, 2013, 11 pages.
Written Submissions from the Patentee, Glaxosmithkline Biologicals SA for EP1645631, dated Feb. 3, 2016, 10 pages.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic Neisseria Conference 2010, p. 109.
Zhu et al. (2004). "Evaluation of the purified recombinant lipidated P2086 protein as a vaccine candidate for group B Neisseria meningitidis in a murine nasal challenge model," 14th International Pathogenic Neisseria Conference 2004, p. 199.
Zhu et al. (2005) "Evaluation of recombinant lipidated P2086 protein as a vaccine candidate for group B Neisseria meningitidis in a murine nasal challenge model," Infect Immun 73(10):6838-45.
Zhu et al. (2006) "Intranasal immunization of mice with recombinant lipidated P2086 protein reduces nasal colonization of group B Neisseria meningitidis," Vaccine 24:5420-5.
Zhu et al. (2006). "Effective immunization strategy against group B Neisseria meningitidis using purified recombinant lipidated P2086 protein," 15th International Pathogenic Neisseria Conference 2006, p. 47.
Zlotnick et al. (2009). "Epidemiology of the serogroup B Neisseria meningitidis (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and antibodies to the fHBP of N. meningitidis," 17th International Pathogenic Neisseria Conference 2010, p. 38.
Zollinger et al. (2010). "Design and evaluation in mice of a broadly protective meningococcal group B native outer membrane vesicle vaccine," Vaccine, 28(31):5057-5067.
Final Office Action dated Jan. 25, 2016 in U.S. Appl. No. 11/587,189. 34 pages.
Response Final Office Action dated Jan. 25, 2016, filed Jun. 23, 2016 in U.S. Appl. No. 11/587,189. 11 pages.
Alignment of SEQ ID No. 42 of EP2258716 with NMA0586, submitted Jul. 29, 2016, filed in opposition against EP2258716, 1 page.

(56) References Cited

OTHER PUBLICATIONS

Alignment of the sequence of strain Z2491 with sequences coding for subfamily A 2086 proteins disclosed by WO 2003/063766, filed in opposition against EP1562983 on Sep. 13, 2016, 36 pages.
Amended Defense and Counterclaim, Appendix II, UK High Court proceedings in *GlaxoSmithKline UK Limited* v. *Wyeth Holdings LLC*, dated Aug. 10, 2015, filed in opposition against EP2258716, 4 pages.
Appendix A, comparison of genes predicted within "contig295" by ORFFinder, filed in relation to EP1645631 on Aug. 15, 2016, 1 page.
Approved Judgment, dated May 12, 2016, UK High Court Decision in *GlaxoSmithKline UK Limited* v. *Wyeth Holdings LLC*, filed in opposition against EP2258716 and EP1562983, 66 pages.
Claimant's Notice of Experiments, UK High Court proceedings in *GlaxoSmithKline UK Limited* v. *Wyeth Holdings LLC*, submitted Jul. 28, 2016 in opposition proceedings against EP2258716 and EP1562983, 8 pages.
Compton (1990). "Degenerate primers for DNA amplification," in "PCR Protocols: A Guide to Methods and Applications," Innis et al. (Eds.), pp. 39-45, Academic Press, San Diego.
Contig 295 from Sanger nm 'old data' ORF Finder, filed in relation to EP1645631, dated Jul. 1, 2013, 9 pages.
Contig 295 ORF Finder, filed in relation to EP1645631, dated Sep. 21, 2012, 2 pages.
Decision of the board of appeal, filed in relation to appeal proceedings for EP1645631, dated Sep. 15, 2016, 37 pages.
Decision revoking EP2258716, filed in opposition against EP2258716, dated Oct. 27, 2016, 15 pages.
Declaration by James Cleland Paton, dated Nov. 24, 2014, 16 pages.
Declaration of Robert Donald, filed in opposition against EP1562983, dated Sep. 12, 2016, 3 pages.
Don et al. (1991). "'Touchdown' PCR to circumvent spurious priming during gene amplification," Nucleic Acids Res. 19(14):4008.
Expert Report of Professor John Heckels, UK High Court proceedings in *GlaxoSmithKline UK Limited* v. *Wyeth Holdings LLC*, dated Jan. 11, 2016, 82 pages.
Fourth declaration of Julian Parkhill, filed in Relation to EP1645631, dated Aug. 25, 2016, 6 pages.
Great Britain Application No. 0121591.2, Filed Sep. 6, 2001, Entitled "Hybrid and tandem expression of neisserial proteins," Applicant Chiron S.p.A., 54 pages.
Great Britain patent application No. 0227346.4, filed Nov. 22, 2003, entitled "741," by applicant Chiron SpA.
Schild et al. (1996). "Peptide Based Vaccines," in "Concepts in Vaccine Development," Kaufmann (Ed.), pp. 303-326, De Gruyter.
Interlocutory decision, filed in opposition against EP1562983, dated Nov. 4, 2016, 16 pages.
Lee et al. (1990). "cDNA Cloning Using Degenerate primers," in "PCR Protocols: A Guide to Methods and Applications," Innis et al. (Eds.), pp. 46-53, Academic Press, San Diego.
MenB sequence ORF Finder, chromosome: ASM880v1:chromosome:1975118:1976280:1, filed in opposition against EP1801219, dated Sep. 27, 2012, 6 pages.
Minutes of the oral proceedings before the board of appeal, filed in opposition against EP1645631, dated Sep. 15, 2016, 5 pages.
NMA0586 (D79b), filed in relation to EP1645631 on Sep. 2, 2016, 9 pages.
Ochman et al. (1990). "Amplification of flanking sequences by inverse PCR," in "PCR Protocols: A Guide to Methods and Applications," Innis et al. (Eds.), pp. 219-227, Academic Press, San Diego.
Patentee's submissions, filed in relation to appeal proceedings for EP1737486, dated Dec. 1, 2016, 5 pages.
Pfizer's submissions in opposition against EP2343308, dated May 2, 2016, filed in opposition against EP1562983, 33 pages.
Response by patentee, dated Jul. 28, 2016, filed in opposition against EP1562983, 4 pages.
Submission by Novartis, filed in opposition against EP2327719, dated Oct. 25, 2016, 9 pages.
Submission by Pfizer in preparation to oral proceedings, filed in opposition against EP2327719, dated Nov. 16, 2016, 7 pages.
Submission by Pfizer, filed in opposition against EP2327719, dated Oct. 25, 2016, 28 pages.
Submissions by opponent, Wyeth LLC, filed in relation to EP1645631, dated Sep. 1, 2016, 19 pages.
Submissions by patentee, GlaxoSmithKline Biologicals SA, filed in relation to EP1645631 on Aug. 15, 2016, 16 pages.
Vu et al. (2012) "A Broadly Cross-Reactive Monoclonal Antibody Against an Epitope on the N-terminus of Meningococcal fHbp" Sci Rep. 2: 341, pp. 1-8.
Zhou et al. (2000). "Universal TA cloning," Curr Issues Mol Biol. 2(1):1-7.
Alignments of SEQ ID Nos. 42-44 of WO2004048404 with SEQ ID No. 24, 33 and 41 of WO2004048404, filed in relation to EP1562983, submitted Mar. 14, 2017 , 5 pages.
Bos et al. (2014), "Involvement of *Neisseria meningitidis* Lipoprotein GNA2091 in the Assembly of a Subset of Outer Membrane Protein," J. Biol. Chem 289(22):15602-610.
Communication from the Examining Division, filed in Opposition against EP2975127, dated Mar. 24, 2017, 4 pages.
Decision in Opposition Proceedings, Filed in opposition against EP1645631, Dated May 30, 2017, 3 pages.
Decision revoking EP2327719 during the opposition of EP2327719, dated Feb. 6, 2017, 18 pages.
Declaration of Dr. Leonard Mayer, filed in relation to EP1562983, dated Mar. 10, 2017, 3 pages.
Declaration of Dr. Loek van Alphen, filed in relation to EP1562983, dated Mar. 11, 2017, 9 pages.
Declaration of Dr. Wendell Zollinger, filed in relation to EP1562983, dated Mar. 13, 2017, 4 pages.
Excerpt of sequence data of 1997-12-15-NM.dbs, Enclosed to fourth declaration of Jullian Parkhill, Filed in opposition against EP1801219, Dated Aug. 22, 2016, 6 pages.
Jongerius et al. (2013) "Distinct binding and immunogenic properties of the gonococcal homologue of meningococcal factor h binding protein," PLOS Palhogens. 9(8):e1003528 pp. 1.
Pajon et al. (2011). "Meningococcal factor H binding proteins in epidemic strains from Africa: implications for vaccine development," PLoS Negl Trop Dis. 5(9):e1302.
Patentee's submission of amended description, filed in relation to post-appeal proceedings for EP1645631, dated Feb. 17, 2017. 19 pages.
Response to notice of opposition, Filed in opposition against EP1801219, Dated Dec. 30, 2016, 6 pages.
Santolaya et al. (2012) "Immunogenicity and tolerability of a multicomponent meningococcal serogroup B (4CMenB) vaccine in healthy adolescents in Chile: a phase 2b/3 randomised, observer-blind, placebo-controlled study," Lancet. 379(9816):617-24.
Serruto et al. (2012). "The new multicomponent vaccine against meningococcal serogroup B, 4CMenB: immunological, functional and structural characterization of the antigens," Vaccine. 30(0 2): B87-B97.
Statement of grounds of appeal, filed in relation to EP1562983, Dated Mar. 14, 2017, 20 pages.
UK High Court Claim Form, Claimant Pfizer, Inc., Defendant *GlaxoSmithKline Biologicals S.A*., submitted Mar. 24, 2017 in opposition against EP1801219, 4 pages.
Vu et al. (2011). "Cooperative serum bactericidal activity between human antibodies to meningococcal factor H binding protein and neisserial heparin binding antigen," Vaccine. 24;29(10):1968-73.
Withdrawal of opposition, filed in relation to EP1562983, dated May 2, 2017, 1 page.
Notice of Appeal by GlaxoSmithKline Biologicals S.A., filed in relation to EP2327719, dated Mar. 24, 2017, 6 pages.
Withdrawal of Opposition by Pfizer Inc., filed in opposition against EP2327719, dated May 2, 2017, 1 page.
Withdrawal of Appeal by patentee, filed in relation to EP2327719, dated May 31, 2017, 1 page.

\* cited by examiner

VACCINES FOR SEROGROUP X MENINGOCOCCUS

CROSS REFERENCE TO RELATED APPLICATIONS

This application is a U.S. National Phase of International Patent Application No. PCT/IB2013/054886 filed Jun. 14, 2013 and published in English, which claims the benefit of U.S. Provisional Application No. 61/659,595, filed Jun. 14, 2012. The entire contents of the foregoing applications are incorporated herein by reference for all purposes.

SEQUENCE LISTING

The instant application contains a Sequence Listing which has been submitted electronically in ASCII format and is hereby incorporated by reference in its entirety. Said ASCII copy, created on Jun. 2, 2015, is named PAT055127-US-PCT_SL.txt and is 37,851 bytes in size.

TECHNICAL FIELD

This invention is in the field of vaccines for immunising against *Neisseria meningitidis* serogroup X.

BACKGROUND ART

Nearly all meningococcal disease is due to strains in serogroups A, B, C, W135 and Y, but serogroup X is also sometimes relevant. There is currently no vaccine for use against serogroup X. Thus there remains a need for a vaccine which would be effective against strains in serogroup X.

DISCLOSURE OF THE INVENTION

The BEXSERO® product (described in references 1 to 4; also known as 4CMenB) has been designed to immunise against serogroup B meningococcus. The inventors have found that patients immunised with BEXSERO® are also protected against strains in serogroup X.

Thus the invention provides a method for immunising a subject against serogroup X meningococcus by administering an immunogenic composition comprising one, two or three of: (i) a meningococcal fHbp antigen; (ii) a meningococcal NHBA antigen; and/or (iii) a meningococcal NadA antigen.

Similarly, the invention provides an immunogenic composition for use in immunising a subject against serogroup X meningococcus, wherein the immunogenic composition comprises one, two or three of: (i) a meningococcal fHbp antigen; (ii) a meningococcal NHBA antigen; and/or (iii) a meningococcal NadA antigen.

Also, the invention provides the use of one, two or three of: (i) a meningococcal fHbp antigen; (ii) a meningococcal NHBA antigen; and/or (iii) a meningococcal NadA antigen, in the manufacture a medicament for immunising a subject against serogroup X meningococcus.

In some embodiments the immunogenic composition also includes meningococcal outer membrane vesicles; in other embodiments the immunogenic composition is free from meningococcal outer membrane vesicles. Where the composition includes meningococcal outer membrane vesicles then the immunogenic composition includes at least one of the fHbp, NHBA and/or NadA antigen(s) in non-OMV form e.g. in soluble form.

Serogroup X Protection

The invention is used to immunise subjects against serogroup X meningococcus, such that recipients of the immunogenic composition mount an immune response which provides protection against infection by and/or disease due to *Neisseria meningitidis* bacteria in serogroup X. This serogroup is characterised by a capsular saccharide having chains of ($\alpha1\rightarrow4$)-linked N-acetylglucosamine 1-phosphate.

Protection against serogroup X strains can be measured epidemiologically, but it is more common and convenient to use an indirect measure such as to confirm that an immunogenic composition elicits a serum bactericidal antibody (SBA) response in recipients. The SBA assay is standard in this field (e.g. see references 5-8) and it shows good inter-laboratory reproducibility when using harmonised procedures [9]. In brief, sera from recipients of the composition are incubated with target bacteria (in the present invention, serogroup X meningococci) in the presence of complement (preferably human complement, although baby rabbit complement is often used instead) and killing of the bacteria is assessed at various dilutions of the sera to determine SBA activity.

It is not necessary that the composition should protect against each and every strain of serogroup X meningococcus, or that each and every recipient of the composition must be protected. Such universal protection is not the normal standard in this field. Rather, protection is normally assessed against a panel of clinically-relevant isolates, often selected on a country-by-country basis and perhaps varying with time, and is measured across a population of recipients. Various serogroup X strains are available for confirming protective efficacy e.g. the composition might protect against M405 (NAMRU#4; ATCC 35560), against strain 860060 (reference strain 657 from the PubMLST database; strain designation X:P1.12-1, 13-5:F5-5: ST-24 (cc750); also known as Z6430), against strains 9557, 9558 &/or 9559 [30], against the serogroup X strains listed in Table 1 of ref 10, against the strains characterised in reference 11, etc.

Within serogroup X, when the immunogenic composition includes a fHbp antigen, the method may be useful for immunising against strains or isolates having the same fHbp variant as the variant in the composition e.g. if the composition includes a variant 1 fHbp then the method will be most useful for immunising against serogroup X strains which express a variant 1 fHbp.

As well as being immunised against serogroup X meningococcus, recipients may also be immunised against other serogroups e.g. one or more of serogroups A, B, C, W135 and/or Y. For instance, reference 12 reports that the antigens in BEXSERO® can protect against serogroup Y, and reference 13 suggests that fHbp might provide protection beyond serogroup B alone.

The Immunogenic Composition

The invention uses an immunogenic composition (e.g. a vaccine) to protect subjects against serogroup X meningococci. The composition includes at least one of fHbp, NHBA and/or NadA antigens, and it elicits an immune response against these included antigens. In some embodiments the composition includes only one of these three antigens (but may include further antigens) e.g. fHBP, NHBA or NadA. In some embodiments the composition includes only two of these three antigens (but may include further antigens) e.g. fHBP+NHBA, fHBP+NadA, NHBA+NadA. In other embodiments the composition includes all three of these three antigens (and may include further antigens).

The composition does not include an immunogenic amount of serogroup X capsular saccharide i.e. protection against serogroup X cannot be explained by an anti-saccharide response. Serogroup X capsular saccharide is absent as free saccharide, conjugated saccharide, or membrane-located saccharide (e.g. in OMVs).

A preferred composition includes each of: (i) a fHbp antigen comprising amino acid sequence SEQ ID NO: 6 e.g. SEQ ID NO: 7; (ii) a NHBA antigen comprising amino acid sequence SEQ ID NO: 8 SEQ ID NO: 9; and (iii) a NadA antigen comprising amino acid sequence SEQ ID NO: 10. BEXSERO® is one such composition.

Although SEQ ID NOs: 6, 8 and 10 are useful amino acid sequences in a combination, the invention is not limited to these precise sequences. Thus 1, 2, or all 3 of these amino acid sequences can independently be modified by up to 5 single amino changes (i.e. 1, 2, 3, 4 or 5 single amino acid substitutions, deletions and/or insertions) provided that the modified sequence can elicit antibodies which still bind to a polypeptide consisting of the unmodified sequence.

The polypeptides in a composition may be present at substantially equal masses i.e. the mass of each of them is within +5% f the mean mass of all the polypeptides. Thus, where the composition includes three polypeptides, one for each of fHbp, HNBA and NadA, they may be present at a mass ratio of a:b:c, where each of a, b & c is between 0.95 and 1.05.

fHbp (Factor H Binding Protein)

The fHbp antigen has been characterised in detail. It has also been known as protein '741' (SEQ IDs 2535 & 2536 in ref. 26), 'NMB1870', 'GNA1870' [14-16], 'P2086', 'LP2086' or 'ORF2086' [17-19], It is naturally a lipoprotein and is expressed across many meningococcal serogroups. The structure of fHbp's C-terminal immunodominant domain ('fHbpC') has been determined by NMR [20], This part of the protein forms an eight-stranded β-barrel, whose strands are connected by loops of variable lengths. The barrel is preceded by a short α-helix and by a flexible N-terminal tail. The protein was confirmed as a factor H binding protein, and named fHbp, in reference 21.

The fHbp antigen falls into three distinct variants [22] and it has been found that serum raised against a given family is bactericidal within the same family, but is not active against strains which express one of the other two families i.e. there is intra-family cross-protection, but not inter-family cross-protection. The invention can use a single fHbp variant, but to provide broader coverage a composition can usefully include a fHbp from two or three of the variants.

Where a composition comprises a single fHBP antigen it may include one of the following:
 (a) a first polypeptide comprising a first amino acid sequence, where the first amino acid sequence comprises an amino acid sequence (i) having at least a % sequence identity to SEQ ID NO: 1 and/or (ii) consisting of a fragment of at least x contiguous amino acids from SEQ ID NO: 1;
 (b) a second polypeptide, comprising a second amino acid sequence, where the second amino acid sequence comprises an amino acid sequence (i) having at least b % sequence identity to SEQ ID NO: 2 and/or (ii) consisting of a fragment of at least y contiguous amino acids from SEQ ID NO: 2;
 (c) a third polypeptide, comprising a third amino acid sequence, where the third amino acid sequence comprises an amino acid sequence (i) having at least c % sequence identity to SEQ ID NO: 3 and/or (ii) consisting of a fragment of at least z contiguous amino acids from SEQ ID NO: 3.

Where a composition comprises two different meningococcal fHBP antigens, it may include a combination of: (i) a first and second polypeptide as defined above; (ii) a first and third polypeptide as defined above; or (iii) a second and third polypeptide as defined above. A combination of a first and third polypeptide is preferred.

In other embodiments a composition comprises three different meningococcal fHBP antigens, with first, second and third polypeptides as defined above.

Where a composition comprises two or three different meningococcal fHBP antigens, although these may share some sequences in common, the first, second and third polypeptides have different fHBP amino acid sequences.

A polypeptide comprising the first amino acid sequence will, when administered to a subject, elicit an antibody response comprising antibodies that bind to the wild-type meningococcus protein having mature amino acid sequence SEQ ID NO: 1 (strain MC58). In some embodiments some or all of these antibodies do not bind to the wild-type meningococcus protein having mature amino acid sequence SEQ ID NO: 2 or to the wild-type meningococcus protein having mature amino acid sequence SEQ ID NO: 3.

A polypeptide comprising the second amino acid sequence will, when administered to a subject, elicit an antibody response comprising antibodies that bind to the wild-type meningococcus protein having mature amino acid sequence SEQ ID NO: 2 (strain 961-5945). In some embodiments some or all of these antibodies do not bind to the wild-type meningococcus protein having mature amino acid sequence SEQ ID NO: 1 or to the wild-type meningococcus protein having mature amino acid sequence SEQ ID NO: 3.

A polypeptide comprising the third amino acid sequence will, when administered to a subject, elicit an antibody response comprising antibodies that bind to the wild-type meningococcus protein having mature amino acid sequence SEQ ID NO: 3 (M1239). In some embodiments some or all of these antibodies do not bind to the wild-type meningococcus protein having mature amino acid sequence SEQ ID NO: 1 or to the wild-type meningococcus protein having mature amino acid sequence SEQ ID NO: 2.

In some embodiments the fragment of at least x contiguous amino acids from SEQ ID NO: 1 is not also present within SEQ ID NO: 2 or within SEQ ID NO: 3. Similarly, the fragment of at least y contiguous amino acids from SEQ ID NO: 2 might not also be present within SEQ ID NO: 1 or within SEQ ID NO: 3. Similarly, the fragment of at least z contiguous amino acids from SEQ ID NO: 3 might not also be present within SEQ ID NO: 1 or within SEQ ID NO: 2. In some embodiments, when said fragment from one of SEQ ID NOs: 1 to 3 is aligned as a contiguous sequence against the other two SEQ ID NOs, the identity between the fragment and each of the other two SEQ ID NOs is less than 75% e.g. less than 70%, less than 65%, less than 60%, etc.

The value of a is at least 80 e.g. 82, 84, 86, 88, 90, 92, 94, 95, 96, 97, 98, 99 or more. The value of b is at least 80 e.g. 82, 84, 86, 88, 90, 92, 94, 95, 96, 97, 98, 99 or more. The value of c is at least 80 82, 84, 86, 88, 90, 92, 94, 95, 96, 97, 98, 99 or more. The values of a, b and c may be the same or different. In some embodiments, a b and c are identical.

The value of x is at least 7 e.g. 8, 9, 10, 11, 12, 13, 14, 15, 16, 17, 18, 19, 20, 21, 22, 23, 24, 25, 26, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 70, 80, 90, 100, 120, 140, 160, 180, 200, 225, 250). The values of x, y and z may be the same or different. In some embodiments, iv and z are identical.

Fragments preferably comprise an epitope from the respective SEQ ID NO: sequence. Other useful fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of the respective SEQ ID NO: while retaining at least one epitope thereof.

Amino acid sequences used with the invention may, compared to SEQ ID NOs: 1 2 or 3, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may have one or more (e.g. 1, 2, 3, 4, 5, 6, 7, 8, 9, 10, etc.) single amino acid deletions relative to a reference sequence. The polypeptides may also include one or more (e.g. 1, 2, 3, 4, 5, 6, 7, 8, 9, 10, etc.) insertions (e.g. each of 1, 2, 3, 4 or 5 amino acids) relative to a reference sequence.

A useful first amino acid sequence has at least 85%) identity (e.g. ≥95% or 100%) to SEQ ID NO: 1. Another useful first amino acid sequence has at least 95% identity (e.g. ≥98%) or 100%) to SEQ ID NO: 12.

A useful third amino acid sequence has at least 85% identity (e.g. ≥95% or 100%) to SEQ ID NO: 3. Another useful third amino acid sequence has at least 95% identity (e.g. ≥98% or 100%) to SEQ ID NO: 11.

Combinations comprising a mixture of first and third sequences based around SEQ ID NOs: 11 and 12 (or their close variants) are particularly useful. Thus a composition may comprise a polypeptide comprising amino acid sequence SEQ ID NO: 11 and a further polypeptide comprising amino acid sequence SEQ ID NO: 12.

Another useful fHbp which can be used with the invention is one of the modified forms disclosed, for example, in reference 23 e.g. comprising SEQ ID NO: 20 or 23 therefrom. These modified forms can use a single fHbp polypeptide to elicit antibody responses which are broadly bactericidal against various fHbp variants. SEQ ID NO: 77 in reference 23 is another useful fHbp sequence which can be used.

fHbp antigens used with the invention can be lipidated e.g. at a N-terminus cysteine residue. In other embodiments they will not be lipidated, and may include amino acid sequences upstream of the natural mature N-terminal cysteine. SEQ ID NOs: 1-3 and 11-12 begin with the cysteine from the natural N-terminus of the relevant mature fHbp polypeptides. For lipidated fHBPs, lipids attached to cysteines will usually include palmitoyl residues e.g. as tripalmitoyl-S-glyceryl-cysteine (Pam3Cys), dipalmitoyl-S-glyceryl cysteine (Pam2Cys), N-acetyl (dipalmitoyl-S-glyceryl cysteine), etc.

Administration of a fHBP will preferably elicit antibodies which can bind to a meningococcal polypeptide consisting of amino acid sequence SEQ ID NO: 1, 2 or 3. Advantageous fHBP antigens for use with the invention can elicit bactericidal anti-meningococcal antibodies after administration to a subject.

The total amount of a fHBP polypeptide will usually be between 1 and 500 µg/dose e.g. between 60 and 200 µg/dose or between 120 and 500 µg/ml.

A polypeptide including the fHbp antigen sequence can include that sequence alone, or it can be a fusion polypeptide. One useful fusion partner for a fHbp sequence is the NMB2091 polypeptide, which will normally be upstream of the fHbp sequence. Thus the fHbp antigen can be present in a composition of the invention as a NMB2091-fHbp fusion e.g. SEQ ID NO: 7.

NHBA (Neisserial Heparin Binding Antigen)

NHBA was included in the published genome sequence for meningococcal serogroup B strain MC58 [24] as gene NMB2132 (GenBank accession number GI:7227388; SEQ ID NO: 4 herein). Sequences of NHBA from many strains have been published since then. For example, allelic forms of NHBA (referred to as protein '287') can be seen in FIGS. 5 and 15 of reference 25, and in example 13 and FIG. 21 of reference 26 (SEQ IDs 3179 to 3184 therein). Various immunogenic fragments of NHBA have also been reported. The protein was confirmed as a heparin binding protein, and named NHBA, in reference 27.

Preferred NHBA antigens for use with the invention comprise an amino acid sequence: (a) having 70% r more identity (e.g. 70%, 75%, 80%, 85%, 90%, 91%, 92%, 93%, 94%, 95%, 96%, 97%, 98%, 99%, 99.5% r more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 35, 40, 50, 60, 70, 80, 90, 100, 150, 200, 250 or more). Preferred fragments of (b) comprise an epitope from SEQ ID NO: 4.

The most useful NHBA antigens can elicit antibodies which, after administration to a subject, can bind to a meningococcal polypeptide consisting of amino acid sequence SEQ ID NO: 4. Advantageous NHBA antigens for use with the invention can elicit bactericidal anti-meningococcal antibodies after administration to a subject.

A polypeptide including the NHBA antigen sequence can include that sequence alone, or it can be a fusion protein. One useful fusion partner for a NHBA sequence is the NMB1030 polypeptide, which will normally be downstream of the NHBA sequence. Thus the NHBA antigen can be present in a composition of the invention as a NHBA-NMB1030 fusion e.g. SEQ ID NO: 9.

NadA (Neisserial Adhesin A)

The NadA antigen was included in the published genome sequence for meningococcal serogroup B strain MC58 [24] as gene NMB1994 (GenBank accession number GI:7227256; SEQ ID NO: 5 The sequences of NadA antigen from many strains have been published since then, and the protein's activity as a Neisserial adhesin has been well documented. Various immunogenic fragments of NadA have also been reported. The protein was confirmed as an adhesin, and named NadA, in reference 28.

Preferred NadA antigens for use with the invention comprise an amino acid sequence: (a) having 70% r more identity (e.g. 70%, 75%, 80%, 85%, 90%, 91%, 92%, 93%, 94%, 95%, 96%, 97%, 98%, 99%, 99.5% r more) to SEQ ID NO: 5; and/or (b) comprising a fragment of at least 'n' consecutive amino acids of SEQ ID NO: 5, wherein 'n' is 7 or more (e.g. 8, 10, 12, 14, 16, 18, 20, 25, 35, 40, 50, 60, 70, 80, 90, 100, 150, 200, 250 or more). Preferred fragments of (b) comprise an epitope from SEQ ID NO: 5.

The most useful NadA antigens can elicit antibodies which, after administration to a subject, can bind to a meningococcal polypeptide consisting of amino acid sequence SEQ ID NO: 5. Advantageous NadA antigens for use with the invention can elicit bactericidal anti-meningococcal antibodies after administration to a subject. SEQ ID NO: 10 is one such fragment.

Outer Membrane Vesicles

In some embodiments the immunogenic composition is free from meningococcal outer membrane vesicles (OMVs). In other embodiments, however, the immunogenic composition includes meningococcal OMVs. In such OMV-containing embodiments the composition includes at least one of fHbp, NHBA and/or NadA antigen in non-OMV form e.g. in soluble form. Thus these compositions are prepared by mixing OMVs with one or more soluble antigen(s), which contrasts with the approach taken in references 29 and 30.

Where a composition includes OMVs, these OMVs can be any proteoliposomic vesicle obtained by disruption of or blebbing from a meningococcal outer membrane to form vesicles therefrom that retain antigens from the outer membrane. Thus this term includes, for instance, OMVs (sometimes referred to as 'blebs'), microvesicles (MVs) and 'native OMVs' ('NOMVs'). Various such vesicles are known in the art (e.g. see references 31 to 45) and any of these can be included within a composition of the invention.

Further Meningococcal Antigens

A composition can include one or more further meningococcal protein antigens, such as HmbR, NspA, NhhA, App, Omp85, TbpA, TbpB, and/or Cu,Zn-superoxide dismutase.

A composition can include one or more meningococcal saccharide antigens, which will typically be conjugated to carrier proteins. Thus, for instance, a composition might include one or more capsular saccharides from serogroups A, C, W135 and/or Y. For instance, the composition might include the conjugates which are present in the MENVEO, MENACTRA, or NIMENRIX products (all of which include conjugated capsular saccharides for each of serogroups A, C, W135 and Y).

Non-Meningococcal Antigens

A composition can include one or more non-meningococcal antigens. For instance, it can include one or more of. (a) an antigen from *Streptococcus pneumoniae*, such as a saccharide (typically conjugated), as in the PREVNAR and SYNFLORIX products; (b) an antigen from hepatitis B virus, such as the surface antigen HBsAg; (c) an antigen from *Bordetella pertussis*, such as pertussis holotoxin (PT) and filamentous haemagglutinin (FHA) from *B. pertussis*, optionally also in combination with pertactin and/or agglutinogens 2 and 3; (d) a diphtheria antigen, such as a diphtheria toxoid; (e) a tetanus antigen, such as a tetanus toxoid; (f) a saccharide antigen from *Haemophilus influenzae* B (Hib), typically conjugated; and/or (g) inactivated poliovirus antigens.

Non-Antigen Components

In addition to its antigens, an immunogenic composition of the invention typically includes a pharmaceutically acceptable carrier, and a thorough discussion of such carriers is available in reference 46.

The pH of a composition is usually between 6 and 8, and more preferably between 6.5 and 7.5 (e.g. about 7). Stable pH may be maintained by the use of a buffer e.g. a Tris buffer, a citrate buffer, phosphate buffer, or a histidine buffer. Thus a composition will generally include a buffer.

A composition may be sterile and/or pyrogen-free. Compositions may be isotonic with respect to humans.

A composition comprises an immunologically effective amount of its antigen(s). An 'immunologically effective amount' is an amount which, when administered to a subject, is effective for eliciting an antibody response against the antigen. This amount can vary depending upon the health and physical condition of the individual to be treated, their age, the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the mass of protein per dose. A dose of 10-500 μg (e.g. 50 μg) per antigen can be useful.

Immunogenic compositions may include an immunological adjuvant. Thus, for example, they may include an aluminium salt adjuvant or an oil-in-water emulsion (e.g. a squalene-in-water emulsion). Suitable aluminium salts include hydroxides (e.g. oxyhydroxides), phosphates (e.g. hydroxyphosphates, orthophosphates), (e.g. see chapters 8 & 9 of ref. 47), or mixtures thereof. The salts can take any suitable form (e.g. gel, crystalline, amorphous, etc.), with adsorption of antigen to the salt being preferred. The concentration of $Al^{+++}$ in a composition for administration to a patient is preferably less than 5 mg/ml e.g. ≤4 mg/ml, ≤3 mg/ml, ≤2 mg/ml, ≤1 mg/ml, etc. A preferred range is between 0.3 and 1 mg/ml. A maximum of 0.85 mg/dose is preferred. Aluminium hydroxide and aluminium phosphate adjuvants are particularly suitable for use with the invention.

Compositions may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Compositions may comprise detergent e.g. a Tween (polysorbate), such as Tween 80. Detergents are generally present at low levels e.g. <0.01%. Compositions may include residual detergent (e.g. deoxycholate) from OMV preparation. The amount of residual detergent is preferably less than 0.4 μg (more preferably less than 0.2 μg) for every μg of meningococcal protein.

If a vaccine includes LOS, the amount of LOS is preferably less than 0.12 μg (more preferably less than 0.05 μg) for every μg of protein.

Compositions may include sodium salts (e.g. sodium chloride) to give tonicity. A concentration of 10±2 mg/ml NaCl is typical e.g. about 9 mg/ml.

Administration of the Composition

Compositions of the invention will generally be administered directly to a patient. Direct delivery may be accomplished by parenteral injection (e.g. subcutaneously, intraperitoneally, intravenously, intramuscularly, or to the interstitial space of a tissue), or by any other suitable route. Intramuscular administration is preferred e.g. to the thigh or the upper arm. Injection may be via a needle (e.g. a hypodermic needle), but needle-free injection may alternatively be used. A typical intramuscular dosage volume is 0.5 ml.

Administration can involve a single dose schedule, but will usually involve a multiple dose schedule. Suitable intervals between priming doses can be routinely determined e.g. between 4-16 weeks, such as one month or two months. BEXSERO® can be administered at ages of 2, 4 & 6 months, or at 2, 3 & 4 months, with a fourth optional dose at 12 months.

The subject who is immunised is a human being, who may be any age e.g. 0-12 months old, 1-5 years old, 5-18 years old, 18-55 years old, or more than 55 years old.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 48-54, etc.

The term "comprising" encompasses "including" as well as "consisting" e.g. a composition "comprising" X may consist exclusively of X or may include something additional e.g. X±Y.

The term "about" in relation to a numerical value x is optional and means, for example, x±10%.

Where the invention concerns an "epitope", this epitope may be a B-cell epitope and/or a T-cell epitope, but will usually be a B-cell epitope. Such epitopes can be identified empirically (e.g. using PEPSCAN [55,56] or similar methods), or they can be predicted (e.g. using the Jameson-Wolf antigenic index [57], matrix-based approaches [58], MAPITOPE [59], TEPITOPE [60,61], neural networks [62], OptiMer & EpiMer [63, 64], ADEPT [65], Tsites [66], hydrophilicity [67], antigenic index [68] or the methods disclosed in references 69-73, etc.). Epitopes are the parts of an antigen that are recognised by and bind to the antigen binding sites of antibodies or T-cell receptors, and they may also be referred to as "antigenic determinants".

References to a percentage sequence identity between two amino acid sequences means that, when aligned, that percentage of amino acids are the same in comparing the two sequences. This alignment and % homology or sequence identity can be determined using software programs known in the art, for example those described in section 7.7.18 of ref. 74. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 75.

The word "substantially" does not exclude "completely" e.g. a composition which is "substantially free" from Y may be completely free from Y. Where necessary, the word "substantially" may be omitted from the definition of the invention.

BRIEF DESCRIPTION OF DRAWINGS

There are no drawings.

MODES FOR CARRYING OUT THE INVENTION

The BEXSERO® product is described in references 1 to 3 and it includes 50 μg of each of NadA (subvariant 3.1), fHbp subvariant 1.1 (as a GNA2091-fHbp fusion protein), and NHBA subvariant 1.2 (as a NHBA-GNA1030 fusion protein), adsorbed onto 1.5 mg aluminium hydroxide, and with 25 μg OMVs from *N. meningitidis* strain NZ98/254.

Eleven MenX strains, isolated between 1995 and 2007 from several countries, were obtained. Their serotype and serosubtype [76], MLST [77] and genotype were as follows:

| Strain | Serotype | Subtype | Clonal complex | PorA VR1 | VR2 | FetA | fHbp | NHBA | nadA |
|---|---|---|---|---|---|---|---|---|---|
| LNP13407 | Non typeable | P1.5 | ST-181 | 5-1 | 10-1 | F4-23 | 1.60 | 358 | − |
| LNP14354 | Non typeable | P1.5 | ST-181 | 5-1 | 10-1 | F4-23 | 1.461 | 358 | − |
| LNP14355 | Non typeable | P1.5 | ST-181 | 5-1 | 10-1 | F4-23 | 1.461 | 358 | − |
| LNP14964 | Non typeable | P1.5 | ST-181 | 5-1 | 10-1 | F4-23 | 1.461 | 358 | − |
| LNP15038 | Non typeable | P1.5 | ST-181 | 5-1 | 10-1 | F4-23 | 1.461 | 358 | − |
| LNP15075 | Non typeable | P1.5 | ST-181 | 5-1 | 10-1 | F4-23 | 1.60 | 358 | + |
| LNP15877 | Non typeable | P1.5 | ST-181 | 5-1 | 10-1 | F4-23 | 1.60 | 358 | − |
| LNP23557 | Non typeable | P1.5 | ST-181 | 5-1 | 10-1 | F4-23 | 1.461 | 358 | − |
| LNP23558 | Non typeable | P1.5 | ST-181 | 5-1 | 10-1 | F4-23 | 1.61 | 359 | − |
| LNP24196 | 4 | P1.12 | None | 12-1 | 16-52 | F3-9 | 2.23 | 51 | + |
| LNP24287 | 4 | P1.16 | ST-750 | 21 | 16 | F5-5 | 3.69 | 129 | − |

The first 9 strains, all non-typeable, in the same clonal complex, and having the same PorA variable region and FetA marker and fHbp subtype (variant 1), were from African countries; the other two strains were isolated in France.

For SBA, sera were obtained from clinical studies before vaccination and after the administration of the BEXSERO® vaccine. For infants, the tested samples were from 40 infants who had received either three immunizations or three immunizations plus one booster. For other age groups, pooled sera were from 12 adolescents or 23 adults vaccinated with two doses. Most of the adults had already received quadrivalent (ACWY) polysaccharide vaccine. A polyclonal rabbit serum against the serogroup X capsular saccharide was used as a positive control.

Human complement was used for the SBA assays, with serum from vaccinated subject (hSBA) and a polyclonal serum used as control. Protection was defined as a titre of 4 for hSBA [78], Vaccine response was scored either as the percentage of hSBA titres of at least 8 for strains that showed a response <4 prior to vaccination, or as 4 fold increase for strains that showed a response of at least 4 to vaccination. SBA titres were as follows:

| Strain | Positive control | Adults Pre- | Post-3 | Adolescents Pre | Post-2 | Infants Pre | Post-3 | Post-4 |
|---|---|---|---|---|---|---|---|---|
| LNP13407 | >4096 | 4 | >128 | <4 | 128 | <2 | 32 | 64 |
| LNP14354 | 2048 | 16 | >128 | 4 | >128 | <2 | >64 | >64 |
| LNP14355 | 2048 | 8 | 64 | 4 | >128 | <2 | >64 | >64 |

|  |  |  |  |  | | Infants | |
|---|---|---|---|---|---|---|---|
|  | Positive | Adults | | Adolescents | | | Post- |
| Strain | control | Pre- | Post-3 | Pre | Post-2 | Pre | Post-3 | 4 |
| LNP14964 | 2048 | <4 | >128 | <4 | >128 | <2 | 32 | >64 |
| LNP15038 | 1024 | 16 | >128 | <4 | >128 | <2 | >64 | >64 |
| LNP15075 | 128 | 4 | 128 | <4 | 32 | <2 | 16 | 16 |
| LNP15877 | 2048 | 4 | >128 | 8 | >128 | <2 | >64 | >64 |
| LNP23557 | 2048 | <4 | 128 | <4 | 64 | <2 | 16 | 32 |
| LNP23558 | >4096 | 16 | >128 | <4 | >128 | <4 | 16 | 64 |
| LNP24196 | 128 | <4 | 4 | <4 | 4 | <2 | 2 | 2 |
| LNP24287 | 1024 | <4 | 4 | <4 | 8 | <2 | <2 | 2 |

Thus all isolates had SBA titres of ≥128 using the polyclonal anti-capsule serum. In infants, all pre-immunisation titers were lower than 8 (the hSBA titre which correlatesd with protection)S. Slightly higher pre-immunisation titres were observed in adolescents and adults.

After vaccination hSBA titres increased in all tested schedules and age groups, against all isolates from Africa. For isolates with a titres of at least 4 before vaccination, a 4-fold increase in hSBA titres was observed in all cases except for the strain LNP14355 (3-fold increase). In contrast to the African strains, the two isolates from France were not killed by the post-immunisation sera, although SBA titers increased in all cases.

Thus the MenX strains involved in meningococcal meningitis (at least for African strains isolated between 1995-2007) can be covered by the 4CMenB BEXSERO® vaccine. Coverage of these isolates was well predicted based on their fHbp variant type.

It will be understood that the invention is described above by way of example only and modifications may be made whilst remaining within the scope and spirit of the invention.

REFERENCES

[1] Bai et al. (2011) *Expert Opin Biol Ther.* 11:969-85.
[2] Su & Snape (2011) *Expert Rev Vaccines* 10:575-88.
[3] Gorringe & Pajon (2012) *Human Vaccines & Immunotherapeutics* 8:1-10.
[4] Giuliani et al. (2006) *PNAS USA* 103:10834-9.
[5] Borrow et al. (2006) *Vaccine.* 24:5093-107.
[6] Rodriguez et al. (2002) *Clin Vaccine Immunol* 9:109-14.
[7] Borrow & Carlone (2001) *Methods in Molecular Medicine* 66:289-304.
[8] Martin et al. (2005) *Vaccine* 23:2218-21.
[9] Borrow et al. (2005) *Clin Diag Lab Immunol* 12:970-6.
[10] Tzeng et al. (2003) *Infect Immun* 71:6712-20.
[11] Gagneux et al. (2002) *Emerging Infect Dis* 8:462-6.
[12] WO2005/102384.
[13] Jiang et al. (2010) *Vaccine* 28:6086-93.
[14] Masignani et al. (2003) *J Exp Med* 197:789-799.
[15] Welsch et al. (2004) *J Immunol* 172:5605-15.
[16] Hou et al. (2005) *J Infect Dis* 192(4):580-90.
[17] WO03/063766.
[18] Fletcher et al. (2004) *Infect Immun* 72:2088-2100.
[19] Zhu et al. (2005) *Infect Immun* 73(10):6838-45.
[20] Cantini et al. (2006) *J. Biol. Chem.* 281:7220-7227
[21] Madico et al. (2006) *J Immunol* 177:501-10.
[22] WO2004/048404
[23] WO2009/104097.
[24] Tettelin et al. (2000) *Science* 287:1809-1815.
[25] WO00/66741.
[26] WO99/57280
[27] Serruto et al. (2010) *PNAS USA* 107:3770-5.
[28] Comaducci et al. (2002) *J Exp Med* 195:1445-54.
[29] Beernink et al. (2009) *J Infect Dis* 199:1360-8.
[30] Pinto et al. (2011) *Vaccine* 29:7752-8.
[31] WO02/09643.
[32] Katial et al. (2002) *Infect. Immun.* 70:702-707.
[33] U.S. Pat. No. 6,180,111.
[34] WO01/34642.
[35] WO2006/046143.
[36] WO2004/019977.
[37] European patent 0011243.
[38] Fredriksen et al. (1991) *NIPH Ann.* 14(2):67-80.
[39] WO01/91788.
[40] WO2005/004908.
[41] WO2011/036562.
[42] Claassen et al. (1996) *Vaccine* 14:1001-8.
[43] de Kleijn et al. (2000) *Vaccine* 18:1456-66.
[44] WO03/105890.
[45] WO2006/024946
[46] Gennaro (2000) *Remington: The Science and Practice of Pharmacy.* 20th edition, ISBN: 0683306472.
[47] *Vaccine Design* . . . (1995) eds. Powell & Newman. ISBN: 030644867X. Plenum.
[48] *Methods In Enzymology* (S. Colowick and N. Kaplan, eds., Academic Press, Inc.)
[49] *Handbook of Experimental Immunology*, Vols. I-IV (D. M. Weir and C. C. Blackwell, eds, 1986, Blackwell Scientific Publications)
[50] Sambrook et al. (2001) *Molecular Cloning: A Laboratory Manual,* 3rd edition (Cold Spring Harbor Laboratory Press).
[51] *Handbook of Surface and Colloidal Chemistry* (Birdi, K. S. ed., CRC Press, 1997)
[52] Ausubel et al. (eds) (2002) *Short protocols in molecular biology,* 5th edition (Current Protocols).
[53] *Molecular Biology Techniques: An Intensive Laboratory Course,* (Ream et al., eds., 1998, Academic Press)
[54] *PCR (Introduction to Biotechniques Series),* 2nd ed. (Newton & Graham eds., 1997, Springer Verlag)
[55] Geysen et al. (1984) *PNAS USA* 81:3998-4002.
[56] Carter (1994) *Methods Mol Biol* 36:207-23.
[57] Jameson, B A et al. 1988, *CABIOS* 4(1): 181-186.
[58] Raddrizzani & Hammer (2000) *Brief Bioinform* 1(2): 179-89.
[59] Bublil et al. (2007) *Proteins* 68(1):294-304.
[60] De Lalla et al. (1999) *J. Immunol.* 163:1725-29.
[61] Kwok et al. (2001) *Trends Immunol* 22:583-88.
[62] Brusic et al. (1998) *Bioinformatics* 14(2): 121-30
[63] Meister et al. (1995) *Vaccine* 13(6):581-91.
[64] Roberts et al. (1996) *AIDS Res Hum Retroviruses* 12(7):593-610.
[65] Maksyutov & Zagrebelnaya (1993) *Comput Appl Biosci* 9(3):291-7.
[66] Feller & de la Cruz (1991) *Nature* 349(6311):720-1.
[67] Hopp (1993) *Peptide Research* 6:183-190.
[68] Welling et al. (1985) *FEBS Lett.* 188:215-218.
[69] Davenport et al. (1995) *Immunogenetics* 42:392-297.
[70] Tsurui & Takahashi (2007) *J Pharmacol Sci.* 105(4): 299-316.
[71] Tong et al. (2001) *Brief Bioinform.* 8(2):96-108.
[72] Schirle et al. (2001) *J Immunol Methods.* 257(1-2):1-16.
[73] Chen et al. (2007) *Amino Acids* 33(3):423-8.
[74] *Current Protocols in Molecular Biology* (F. M. Ausubel et al., eds., 1987) Supplement 30
[75] Smith & Waterman (1981) *Adv. Appl. Math.* 2: 482-489.
[76] Abdillahi & Poolman (1988) *Microb Pathog* 4:27-32
[77] Harrison et al. (2011) *Microbiology* 157:2181-95.
[78] Frasch et al. (2009) *Vaccine* 27:B112-6.

The invention claimed is:

1. A method for immunizing a subject in need thereof against serogroup X meningococcus by administering to the subject a composition comprising a meningococcal fHbp antigen and an aluminum salt adjuvant; wherein the meningococcal fHbp antigen comprises amino acid sequence SEQ ID NO: 7, wherein the composition either (a) is free from meningococcal outer membrane vesicles or (b) includes meningococcal outer membrane vesicles, and the fHbp antigen is present in the composition in soluble form, wherein the fHbp antigen is not conjugated to a meningococcal polysaccharide, and wherein the composition does not contain un-conjugated meningococcal polysaccharides.

2. The method of claim 1, wherein the composition further comprises one or both of (i) a meningococcal NHBA antigen, and (ii) a meningococcal NadA antigen.

3. The method of claim 2, wherein the composition includes the meningococcal outer membrane vesicles and the meningococcal NHBA antigen, the meningococcal NadA antigen, or both are present in the composition in soluble form.

4. The method of claim 2, wherein the meningococcal NHBA antigen comprises (a) an amino acid sequence at least 95% identical to SEQ ID NO: 4.

5. The method of claim 2, wherein the meningococcal NadA antigen comprises (a) an amino acid sequence at least 95% identical to SEQ ID NO: 5.

6. The method of claim 1, wherein the composition includes each of: (i) an antigen comprising amino acid sequence of SEQ ID NO: 8; and (ii) an antigen comprising amino acid sequence of SEQ ID NO: 10.

7. The method of claim 1, wherein the composition includes each of: (i) an antigen comprising amino acid sequence SEQ ID NO: 9; and (ii) an antigen comprising amino acid sequence SEQ ID NO: 10.

8. The method of claim 2, wherein the antigens are present at substantially equal masses.

9. The method of claim 1, wherein the composition further comprises one or more additional meningococcal protein antigens.

10. The method of claim 1, where the administration induces an immune response against one or more of meningococcal serogroups A, B, C, W135, and Y.

11. The method of claim 1, wherein the composition further comprises one or more non-meningococcal antigens.

12. The method of claim 1, wherein the administration is by intramuscular injection.

13. The method of claim 1, wherein the subject is a human and the human has (i) a 4 fold increase in human serum bactericidal antibody (hSBA) titer after administration if the subject had at least an hSBA titer of 4 before administration, or (ii) an hSBA titer of 8 after administration if the subject had an hSBA titer of less than 4 before administration.

* * * * *

SEQUENCE LISTING

<160> NUMBER OF SEQ ID NOS: 12

<210> SEQ ID NO 1
<211> LENGTH: 255
<212> TYPE: PRT
<213> ORGANISM: Neisseria meningitidis

<400> SEQUENCE: 1

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 2
<211> LENGTH: 254
<212> TYPE: PRT
<213> ORGANISM: Neisseria meningitidis

<400> SEQUENCE: 2

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
            85                  90                  95

Gln Ile Tyr Lys Gln Asp His Ser Ala Val Ala Leu Gln Ile Glu
            100                 105                 110

Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 3
<211> LENGTH: 262
<212> TYPE: PRT
<213> ORGANISM: Neisseria meningitidis

<400> SEQUENCE: 3

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys

```
                    180                 185                 190
Thr Leu Glu Gln Asn Val Glu Leu Ala Ala Glu Leu Lys Ala Asp
            195                 200                 205

Glu Lys Ser His Ala Val Ile Leu Gly Asp Thr Arg Tyr Gly Ser Glu
        210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
                260

<210> SEQ ID NO 4
<211> LENGTH: 488
<212> TYPE: PRT
<213> ORGANISM: Neisseria meningitidis

<400> SEQUENCE: 4

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285
```

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 5
<211> LENGTH: 364
<212> TYPE: PRT
<213> ORGANISM: Neisseria meningitidis

<400> SEQUENCE: 5

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
                20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
        50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Thr Lys Gln Asn Val Asp Ala Lys Val Lys
        210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
            275                 280                 285

Thr Arg Gln Gly Leu Ala Glu Gln Ala Ala Leu Ser Gly Leu Phe Gln
            290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
            355                 360

<210> SEQ ID NO 6
<211> LENGTH: 248
<212> TYPE: PRT
<213> ORGANISM: Neisseria meningitidis

<400> SEQUENCE: 6

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys

```
            180                 185                 190
Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
            210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 7
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fusion protein of fHbp

<400> SEQUENCE: 7

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asp Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Arg Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
```

```
            275                 280                 285
Gln Thr Glu Gln Ile Gln Asp Ser Glu His Ser Gly Lys Met Val Ala
    290                 295                 300

Lys Arg Gln Phe Arg Ile Gly Asp Ile Ala Gly His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
        355                 360                 365

Asn Val Asp Leu Ala Ala Ala Asp Ile Lys Pro Asp Gly Lys Arg His
    370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 8
<211> LENGTH: 468
<212> TYPE: PRT
<213> ORGANISM: Neisseria meningitidis

<400> SEQUENCE: 8

Ser Pro Asp Val Lys Ser Ala Asp Thr Leu Ser Lys Pro Ala Ala Pro
1               5                   10                  15

Val Val Ser Glu Lys Glu Thr Glu Ala Lys Glu Asp Ala Pro Gln Ala
            20                  25                  30

Gly Ser Gln Gly Gln Gly Ala Pro Ser Ala Gln Gly Gly Gln Asp Met
        35                  40                  45

Ala Ala Val Ser Glu Glu Asn Thr Gly Asn Gly Ala Ala Ala Thr
    50                  55                  60

Asp Lys Pro Lys Asn Glu Asp Glu Gly Ala Gln Asn Asp Met Pro Gln
65                  70                  75                  80

Asn Ala Ala Asp Thr Asp Ser Leu Thr Pro Asn His Thr Pro Ala Ser
                85                  90                  95

Asn Met Pro Ala Gly Asn Met Glu Asn Gln Ala Pro Asp Ala Gly Glu
            100                 105                 110

Ser Glu Gln Pro Ala Asn Gln Pro Asp Met Ala Asn Thr Ala Asp Gly
        115                 120                 125

Met Gln Gly Asp Asp Pro Ser Ala Gly Gly Glu Asn Ala Gly Asn Thr
    130                 135                 140

Ala Ala Gln Gly Thr Asn Gln Ala Glu Asn Asn Gln Thr Ala Gly Ser
145                 150                 155                 160

Gln Asn Pro Ala Ser Ser Thr Asn Pro Ser Ala Thr Asn Ser Gly Gly
                165                 170                 175

Asp Phe Gly Arg Thr Asn Val Gly Asn Ser Val Val Ile Asp Gly Pro
            180                 185                 190

Ser Gln Asn Ile Thr Leu Thr His Cys Lys Gly Asp Ser Cys Ser Gly
        195                 200                 205

Asn Asn Phe Leu Asp Glu Glu Val Gln Leu Lys Ser Glu Phe Glu Lys
```

```
            210                 215                 220
Leu Ser Asp Ala Asp Lys Ile Ser Asn Tyr Lys Lys Asp Gly Lys Asn
225                 230                 235                 240

Asp Gly Lys Asn Asp Lys Phe Val Gly Leu Val Ala Asp Ser Val Gln
                245                 250                 255

Met Lys Gly Ile Asn Gln Tyr Ile Ile Phe Tyr Lys Pro Lys Pro Thr
            260                 265                 270

Ser Phe Ala Arg Phe Arg Arg Ser Ala Arg Ser Arg Arg Ser Leu Pro
                275                 280                 285

Ala Glu Met Pro Leu Ile Pro Val Asn Gln Ala Asp Thr Leu Ile Val
            290                 295                 300

Asp Gly Glu Ala Val Ser Leu Thr Gly His Ser Gly Asn Ile Phe Ala
305                 310                 315                 320

Pro Glu Gly Asn Tyr Arg Tyr Leu Thr Tyr Gly Ala Glu Lys Leu Pro
                325                 330                 335

Gly Gly Ser Tyr Ala Leu Arg Val Gln Gly Glu Pro Ser Lys Gly Glu
                340                 345                 350

Met Leu Ala Gly Thr Ala Val Tyr Asn Gly Glu Val Leu His Phe His
            355                 360                 365

Thr Glu Asn Gly Arg Pro Ser Pro Ser Arg Gly Arg Phe Ala Ala Lys
            370                 375                 380

Val Asp Phe Gly Ser Lys Ser Val Asp Gly Ile Ile Asp Ser Gly Asp
385                 390                 395                 400

Gly Leu His Met Gly Thr Gln Lys Phe Lys Ala Ala Ile Asp Gly Asn
                405                 410                 415

Gly Phe Lys Gly Thr Trp Thr Glu Asn Gly Gly Asp Val Ser Gly
                420                 425                 430

Lys Phe Tyr Gly Pro Ala Gly Glu Val Ala Gly Lys Tyr Ser Tyr
                435                 440                 445

Arg Pro Thr Asp Ala Glu Lys Gly Gly Phe Gly Val Phe Ala Gly Lys
450                 455                 460

Lys Glu Gln Asp
465

<210> SEQ ID NO 9
<211> LENGTH: 644
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fusion protein of NHBA

<400> SEQUENCE: 9

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
```

```
                    85                  90                  95
Ala Ser Asn Met Pro Ala Gly Asn Met Glu Asn Gln Ala Pro Asp Ala
                100                 105                 110

Gly Glu Ser Glu Gln Pro Ala Asn Gln Pro Asp Met Ala Asn Thr Ala
                115                 120                 125

Asp Gly Met Gln Gly Asp Pro Ser Ala Gly Glu Asn Ala Gly
                130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
                180                 185                 190

Gly Pro Ser Gln Asn Ile Thr Leu Thr His Cys Lys Gly Asp Ser Cys
                195                 200                 205

Ser Gly Asn Asn Phe Leu Asp Glu Glu Val Gln Leu Lys Ser Glu Phe
                210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
                260                 265                 270

Pro Thr Ser Phe Ala Arg Phe Arg Arg Ser Ala Arg Ser Arg Arg Ser
                275                 280                 285

Leu Pro Ala Glu Met Pro Leu Ile Pro Val Asn Gln Ala Asp Thr Leu
                290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
                340                 345                 350

Gly Glu Met Leu Ala Gly Thr Ala Val Tyr Asn Gly Glu Val Leu His
                355                 360                 365

Phe His Thr Glu Asn Gly Arg Pro Ser Pro Ser Arg Gly Arg Phe Ala
                370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
                420                 425                 430

Ser Gly Lys Phe Tyr Gly Pro Ala Gly Glu Glu Val Ala Gly Lys Tyr
                435                 440                 445

Ser Tyr Arg Pro Thr Asp Ala Glu Lys Gly Gly Phe Gly Val Phe Ala
                450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
                500                 505                 510
```

Phe Asp Gln Ala Lys Arg Asp Gly Lys Ile Asp Ile Thr Ile Pro Val
            515                 520                 525

Ala Asn Leu Gln Ser Gly Ser Gln His Phe Thr Asp His Leu Lys Ser
    530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
    610                 615                 620

Val Asn Val Gly Met Thr Lys Ser Val Arg Ile Asp Ile Gln Ile Glu
625                 630                 635                 640

Ala Ala Lys Gln

<210> SEQ ID NO 10
<211> LENGTH: 327
<212> TYPE: PRT
<213> ORGANISM: Neisseria meningitidis

<400> SEQUENCE: 10

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
            85                  90                  95

Thr Lys Leu Ala Asp Thr Asp Ala Ala Leu Ala Asp Thr Asp Ala Ala
        100                 105                 110

Leu Asp Ala Thr Thr Asn Ala Leu Asn Lys Leu Gly Glu Asn Ile Thr
    115                 120                 125

Thr Phe Ala Glu Glu Thr Lys Thr Asn Ile Val Lys Ile Asp Glu Lys
130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
            165                 170                 175

Val Lys Thr Ala Asn Glu Ala Lys Gln Thr Ala Glu Glu Thr Lys Gln
        180                 185                 190

Asn Val Asp Ala Lys Val Lys Ala Ala Glu Thr Ala Ala Gly Lys Ala
    195                 200                 205

Glu Ala Ala Ala Gly Thr Ala Asn Thr Ala Ala Asp Lys Ala Glu Ala
210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
            245                 250                 255

Glu Ser Asp Ser Lys Phe Val Arg Ile Asp Gly Leu Asn Ala Thr Thr
        260                 265                 270

Glu Lys Leu Asp Thr Arg Leu Ala Ser Ala Glu Lys Ser Ile Ala Asp
    275                 280                 285

His Asp Thr Arg Leu Asn Gly Leu Asp Lys Thr Val Ser Asp Leu Arg
290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
            325

<210> SEQ ID NO 11
<211> LENGTH: 261
<212> TYPE: PRT
<213> ORGANISM: Neisseria meningitidis

<400> SEQUENCE: 11

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
 50                 55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

```
<210> SEQ ID NO 12
<211> LENGTH: 260
<212> TYPE: PRT
<213> ORGANISM: Neisseria meningitidis

<400> SEQUENCE: 12

Cys Ser Ser Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
            115                 120                 125

Val Ala Lys Arg Arg Phe Arg Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
            195                 200                 205

His His Ala Val Ile Ser Gly Ser Val Leu Tyr Asn Gln Asp Glu Lys
    210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
            245                 250                 255

Ala Ala Lys Gln
            260
```